(12) United States Patent
Newsam et al.

(10) Patent No.: US 8,277,762 B2
(45) Date of Patent: Oct. 2, 2012

(54) APPARATUS AND METHODS FOR EVALUATING THE BARRIER PROPERTIES OF A MEMBRANE

(75) Inventors: John M. Newsam, San Diego, CA (US);
Ilya Feygin, Mountainside, NJ (US);
Samir Mitragotri, Goleta, CA (US);
Robert Dominic King-Smith, San Diego, CA (US)

(73) Assignee: Tioga Research, Inc., San Diego, CA (US)

( * ) Notice: Subject to any disclaimer, the term of this patent is extended or adjusted under 35 U.S.C. 154(b) by 1298 days.

(21) Appl. No.: 10/566,648

(22) PCT Filed: Jul. 30, 2004

(86) PCT No.: PCT/US2004/024760
§ 371 (c)(1),
(2), (4) Date: Aug. 16, 2006

(87) PCT Pub. No.: WO2005/012549
PCT Pub. Date: Feb. 10, 2005

(65) Prior Publication Data
US 2007/0183936 A1    Aug. 9, 2007

Related U.S. Application Data

(60) Provisional application No. 60/491,553, filed on Aug. 1, 2003.

(51) Int. Cl.
*B01L 3/00* (2006.01)
(52) U.S. Cl. ........ 422/552; 422/547; 422/548; 422/551; 422/553; 422/559; 436/178
(58) Field of Classification Search ............... 422/82.01, 422/83, 102, 547, 548, 551, 552, 553, 559, 422/560, 561; 436/149, 174, 181, 178
See application file for complete search history.

(56) References Cited

U.S. PATENT DOCUMENTS
4,493,815 A * 1/1985 Fernwood et al. ............ 422/101
(Continued)

FOREIGN PATENT DOCUMENTS
GB    2246081 A    1/1992
(Continued)

OTHER PUBLICATIONS

Supplementary Partial European Search Report dated Aug. 17, 2007 issued in respect of corresponding Application No. EP 04 77 9728.
Supplementary European Search Report dated Jun. 11, 2008 issued in respect of corresponding Application No. EP 04 77 9728.
Examiner's Report dated Sep. 2, 2010 issued in respect of corresponding Application No. CA 2,534,359.

*Primary Examiner* — Jill Warden
*Assistant Examiner* — Dwayne K Handy
(74) *Attorney, Agent, or Firm* — Foley & Lardner LLP

(57) ABSTRACT

The present invention teaches apparatus (511) and methods for screening the effect of test formulations on the barrier properties of a membrane (212), that are especially beneficial when skin is used as the test membrane (212). The apparatus (511) and methods enable more efficient measurements of skin permeabilization, of the permeation of molecular or particulate entities through skin, and of the absorption and adsorption by skin of ingredients in fluid formulations, together with screening of exfoliation of material from the exterior of the stratum corneum. The apparatus (511) provide for fluid contact to the skin from both donor and receptor sides, for measurements of skin electrical response in the presence of test formulations, of permeation and permeation enhancement, for the depth profiling of test formulation constituents through the skin, of stratum corneum component disruption, and of loss of material from the stratum corneum.

27 Claims, 14 Drawing Sheets

U.S. PATENT DOCUMENTS

| | | |
|---|---|---|
| 5,141,719 A | 8/1992 | Fernwood et al. |
| 5,342,581 A | 8/1994 | Sanadi |
| 5,888,830 A * | 3/1999 | Mohan et al. ............... 436/174 |
| 6,045,755 A * | 4/2000 | Lebl et al. .................... 506/33 |
| 6,338,802 B1 | 1/2002 | Bodner et al. |
| 6,455,007 B1 | 9/2002 | Mansky et al. |
| 6,485,690 B1 * | 11/2002 | Pfost et al. ................... 422/552 |
| 6,742,659 B2 | 6/2004 | Clark et al. |
| 6,805,842 B1 * | 10/2004 | Bodner et al. ............... 422/102 |
| 6,817,558 B1 | 11/2004 | Karlsson et al. |
| 7,494,622 B2 * | 2/2009 | Picollet-Dahan et al. . 422/82.01 |
| 2001/0042710 A1 | 11/2001 | Clark et al. |
| 2002/0006643 A1 * | 1/2002 | Kayyem et al. .............. 435/91.2 |
| 2005/0260101 A1 * | 11/2005 | Nauck et al. ................... 422/99 |

FOREIGN PATENT DOCUMENTS

| | | |
|---|---|---|
| WO | 9839099 A1 | 9/1998 |
| WO | 0025922 A2 | 5/2000 |
| WO | 03008112 A1 | 1/2003 |

* cited by examiner

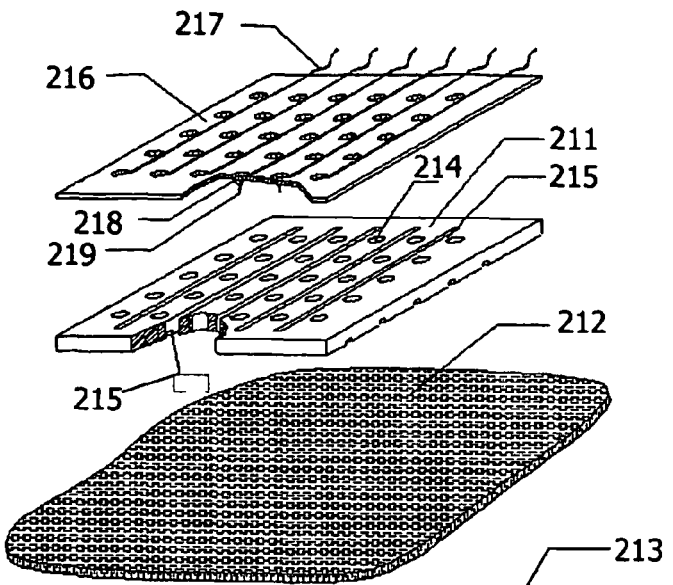
FIG. 2A
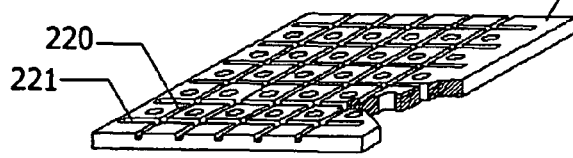
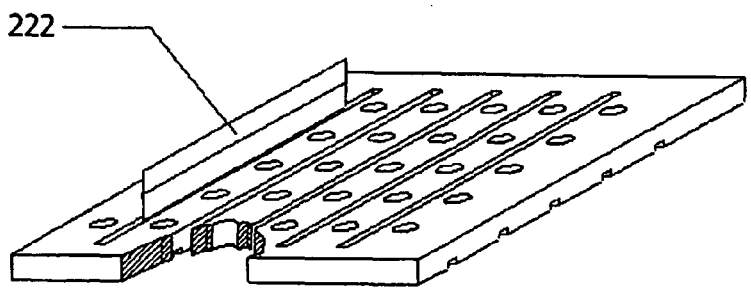
FIG. 2B
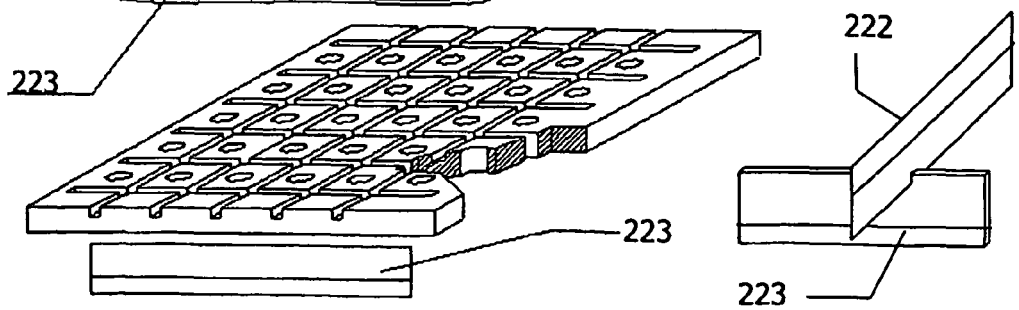

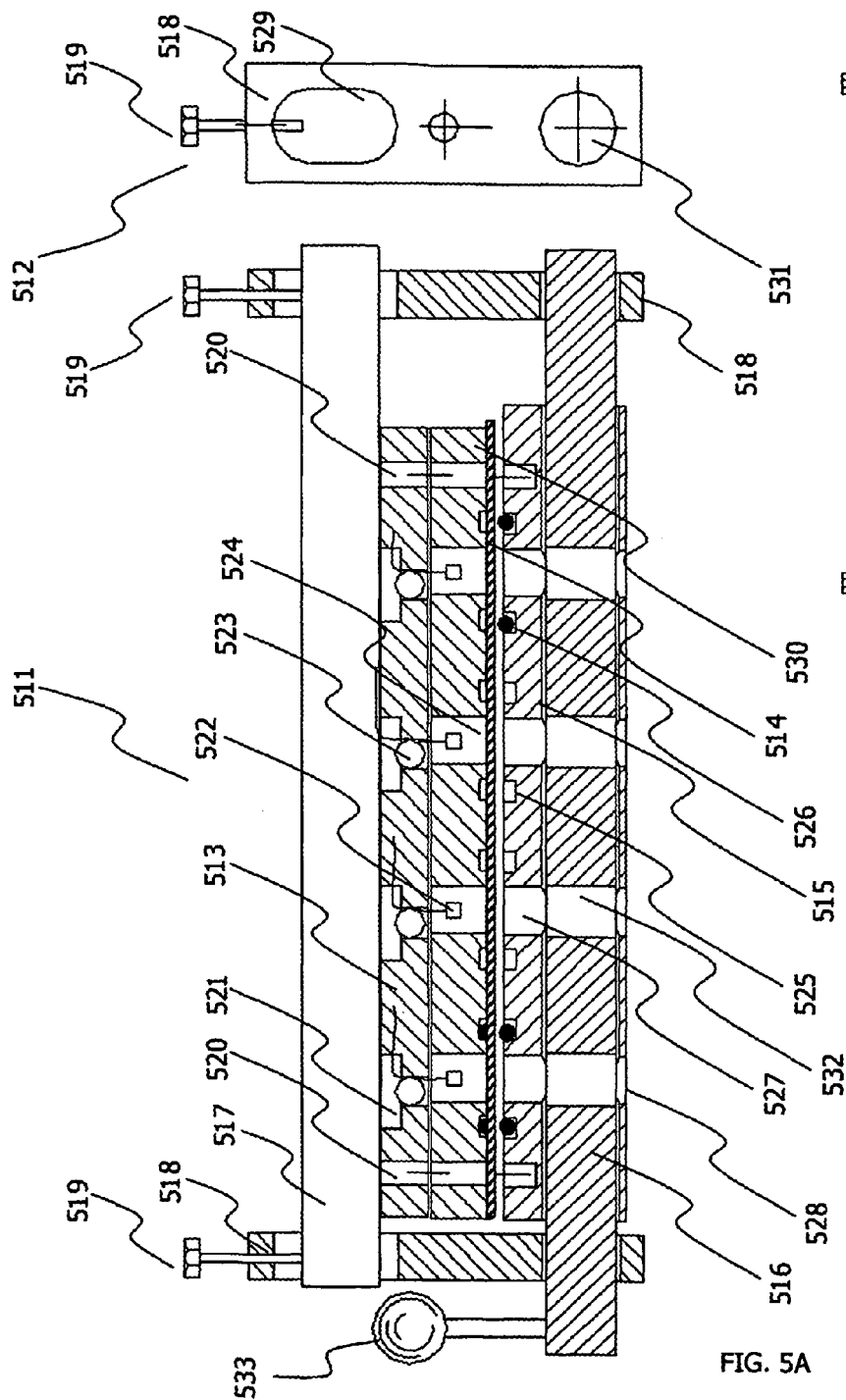
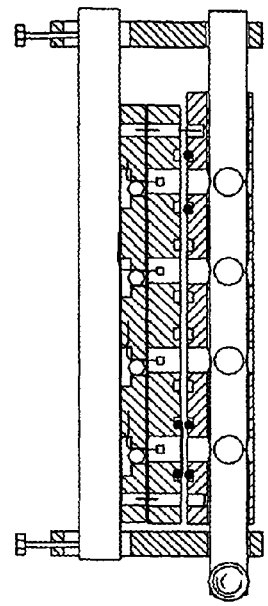
FIG. 5A
FIG. 5B

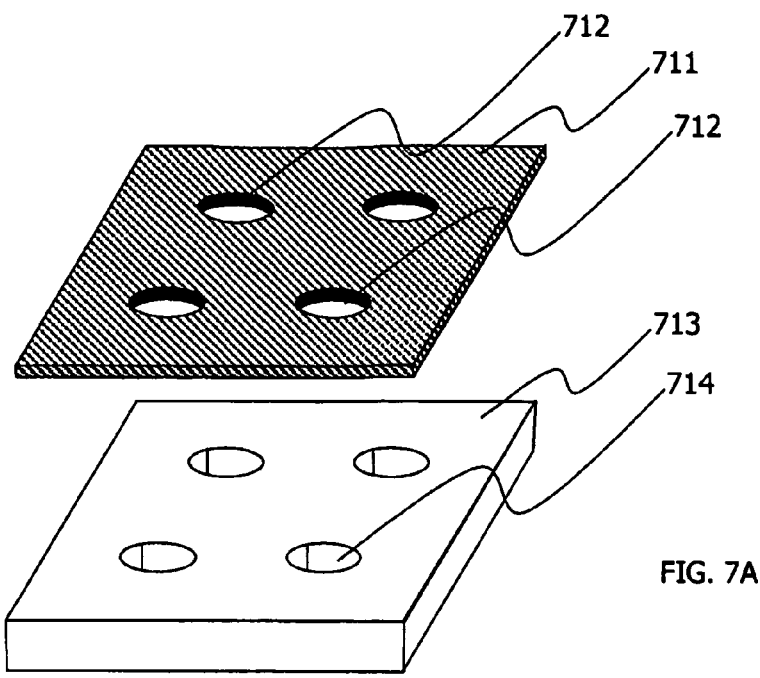
FIG. 7A
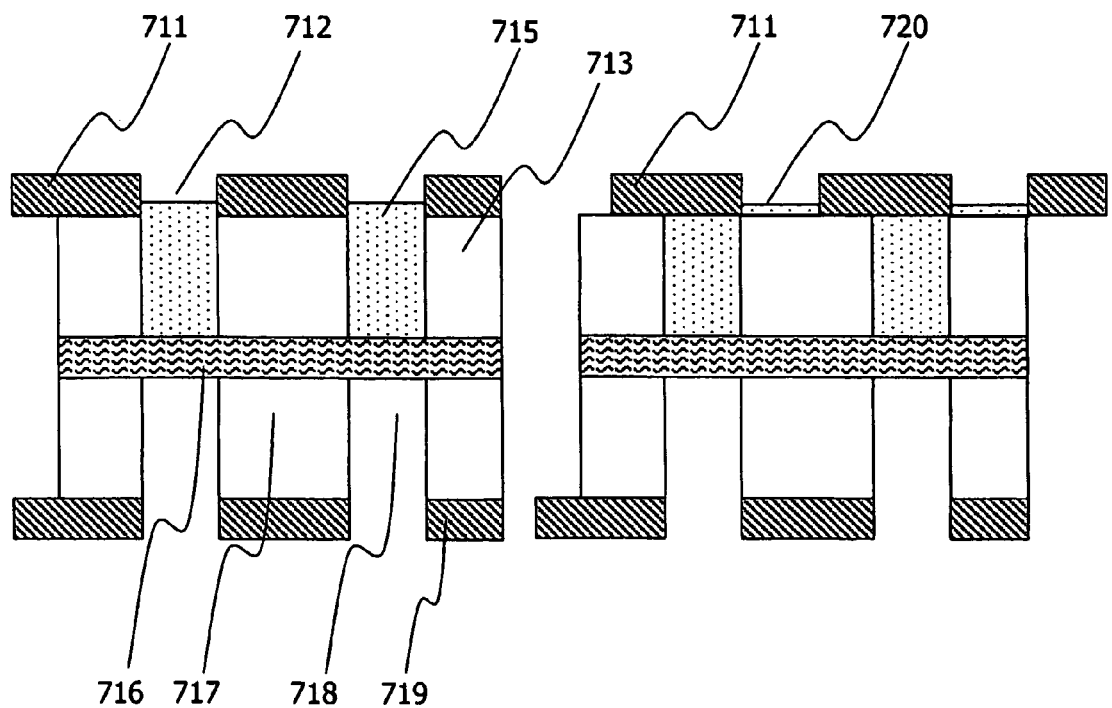
FIG. 7B
FIG. 7C
FIG. 7

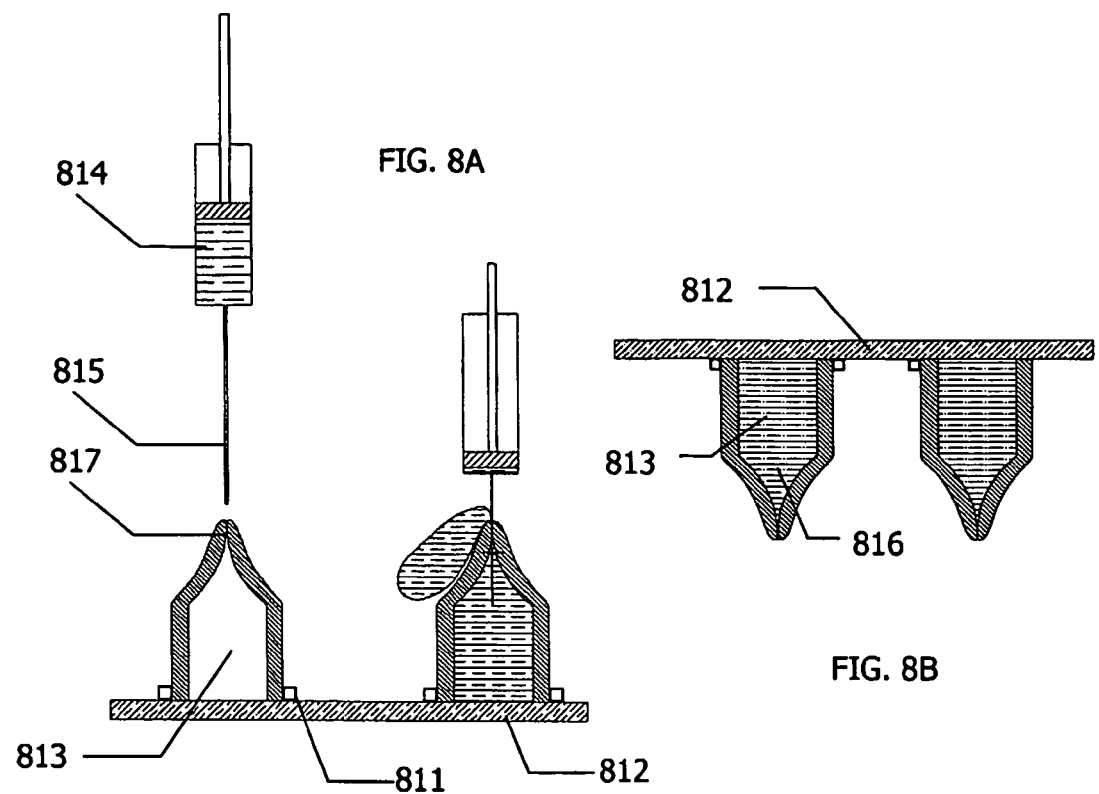
FIG. 8A
FIG. 8B
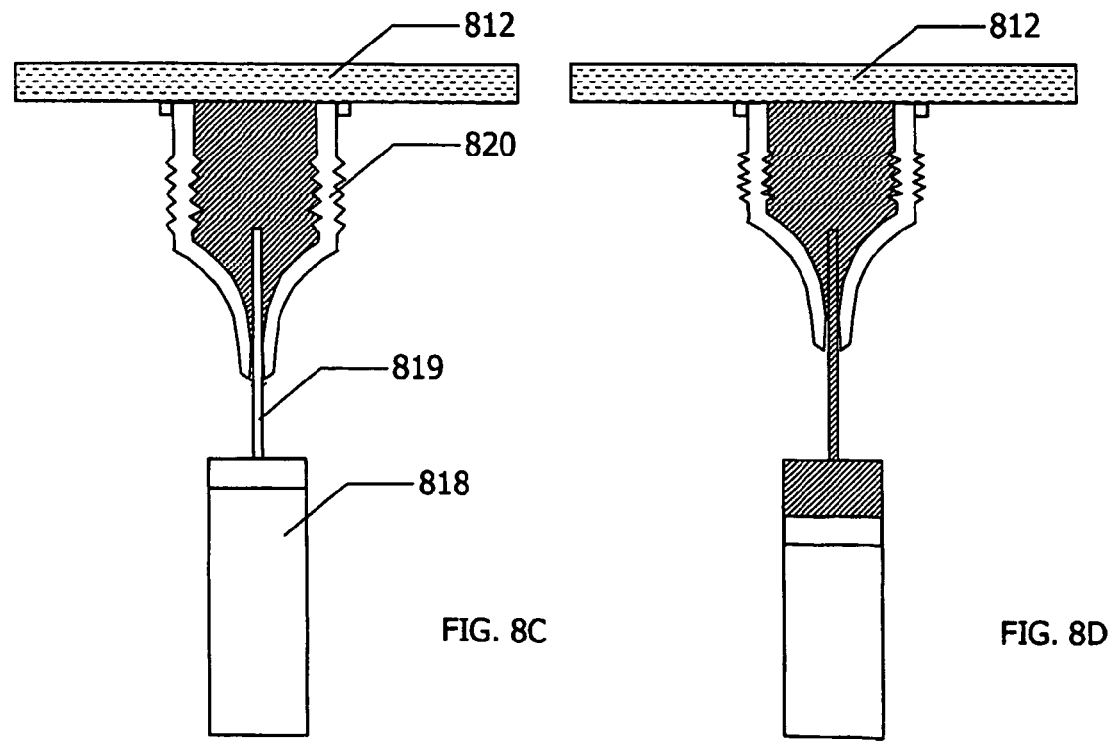
FIG. 8C
FIG. 8D

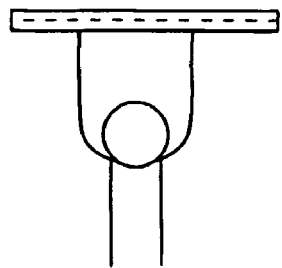
FIG. 9A
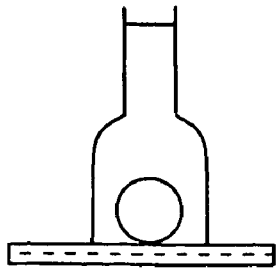
FIG. 9B
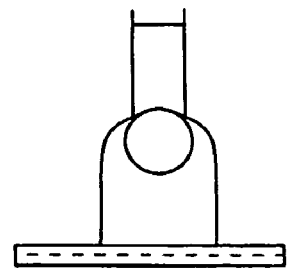
FIG. 9C
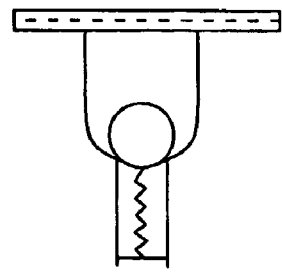
FIG. 9D
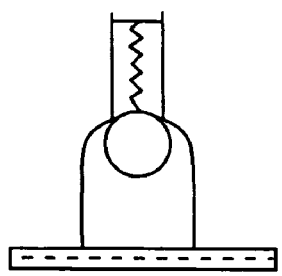
FIG. 9E
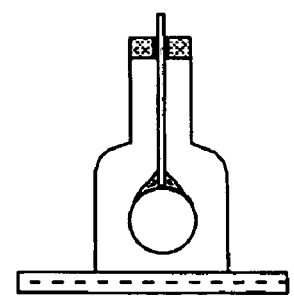
FIG. 9F
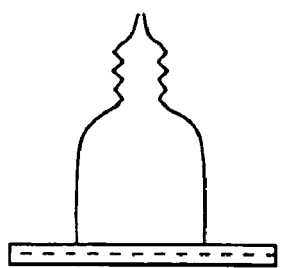
FIG. 9G
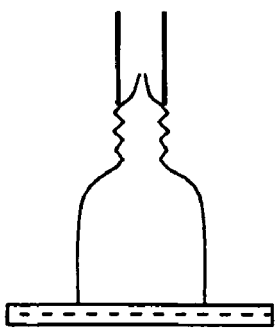
FIG. 9H
FIG. 9

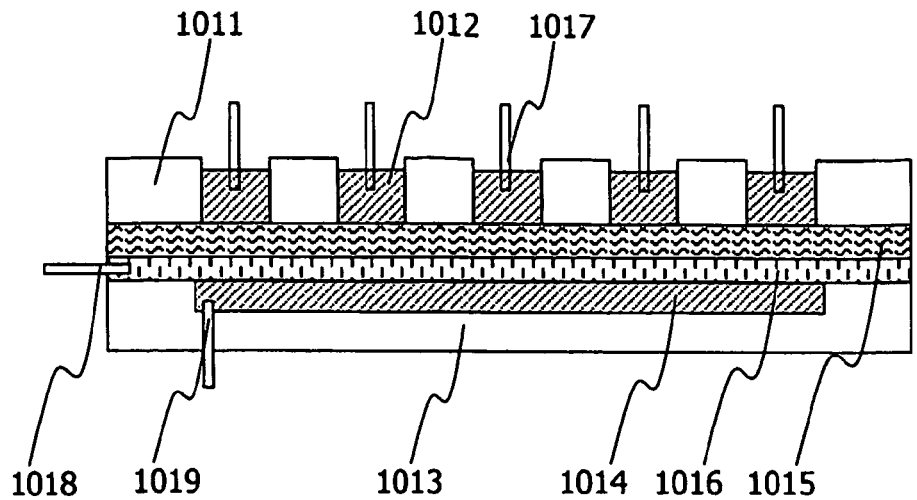
FIG. 10A
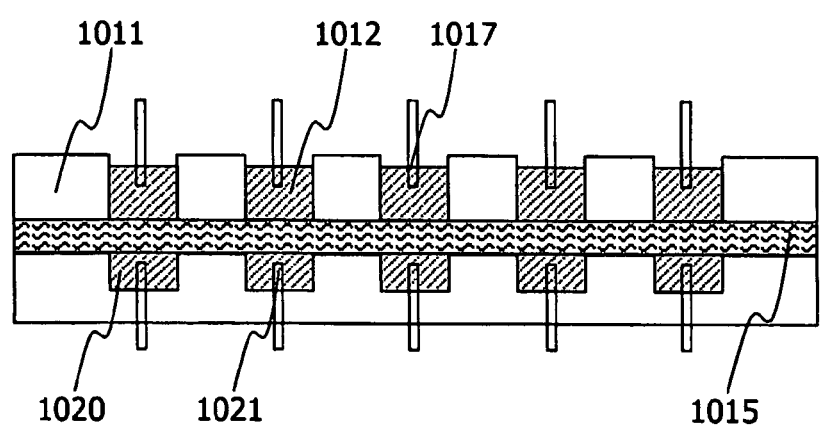
FIG. 10B
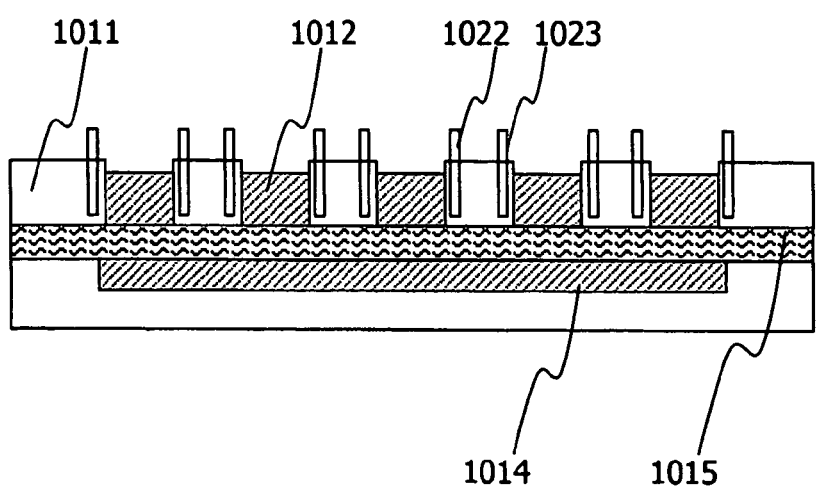
FIG. 10C
FIG. 10

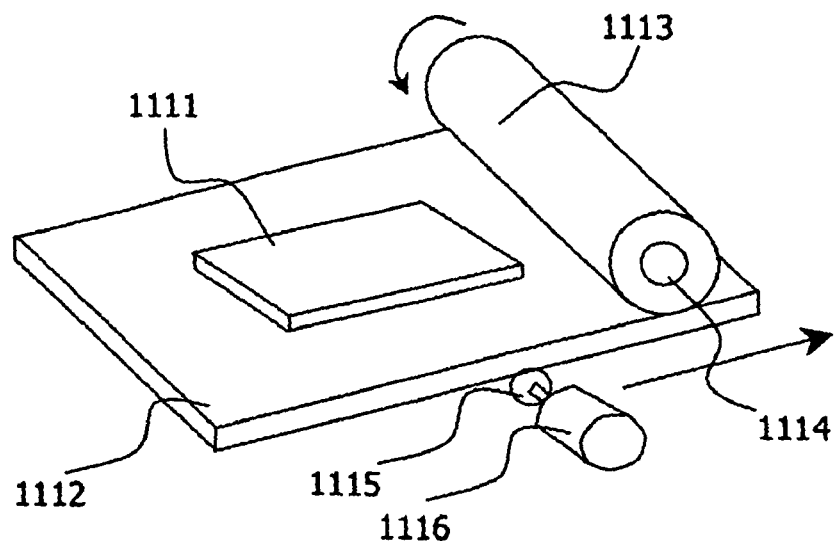
FIG. 11A
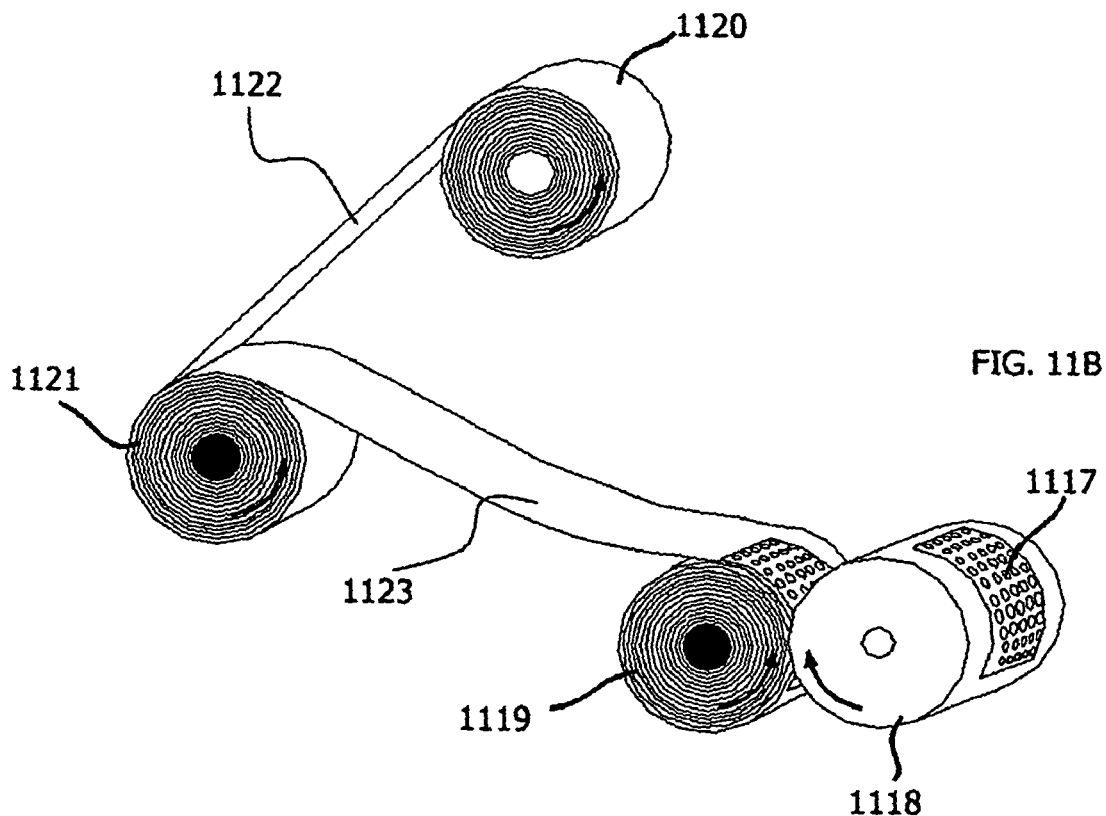
FIG. 11B
FIG. 11

APPARATUS AND METHODS FOR EVALUATING THE BARRIER PROPERTIES OF A MEMBRANE

CROSS-REFERENCE TO RELATED APPLICATIONS

This application claims the benefit of Provisional Application No. 60/491,553, filed on Aug. 1, 2003, which is incorporated herein by reference.

FIELD OF THE INVENTION

The present invention relates generally to the development of methods for modifying the barrier properties of a membrane, such as skin, and to rapid and efficient methods of measuring the effect of chemicals on the barrier properties.

BACKGROUND OF THE INVENTION

Membranes, both natural and synthetic, play critical roles in many fields. The utility of such membranes depends on a number of factors, physical, mechanical, chemical and biological. In many cases, of central issues are the barrier properties of the membrane, which determine the degree to and rate at which species of various types can pass through the membrane. It is often desirable to modify these barrier properties for the specific use. One of the most evident of natural membranes is skin.

Skin as a Barrier

The skin, the largest organ of the human body, has three layers—the epidermis, dermis and subcutis. The subcutis, the deepest layer, provides thermal insulation and has a shock-absorbing effect that helps protect the body's organs from injury. The dermis, the middle layer, contains hair shafts, sweat glands, blood vessels and nerves. The top layer of the skin is the epidermis, separated from the other layers of skin by the basement membrane which serves as the "glue" at the dermal-epidermal junction. The epidermis is relatively thin, and it is divided into four layers, from the innermost to outermost: the basal cell layer, stratum spinosum, stratum granulosum, and stratum corneum. The basal cell layer contains basal cells which divide and differentiate into other cells in the epidermis, and melanocytes, the cells that make melanin which gives skin its color. The stratum spinosum lies outside the basal cell layer and is comprised of keratinocytes, cells that make the protein keratin, an important component of the stratum corneum as well as of hair and nails. Cells in the stratum granulosum are flattened and contain dark granules that are expelled and provide the "cement" that holds cells together in the overlying stratum corneum. The stratum corneum, the outermost layer of the epidermis, is only some 20 µm thick, yet contributes over 80% to the skin permeability barrier. It is comprised of overlapping, flat corneocytes organized in columnar clusters; the clusters are sealed with multi-lamellar lipid sheets that are covalently attached to the cell membranes and are tightly packed. The stratum corneum is thicker in areas like the palms and soles that withstand more daily wear and tear than those of other parts of the body. The epidermis also contains Langerhans cells, which act as part of the skin's defense against infection.

Skin serves as the body's natural barrier against incursion of chemical or pathogenic factors, but it is a dynamic environment and there is major commercial interest in developing ways in which the barrier properties of skin can be modified.

Delivery through the Skin: A transdermal delivery route for therapeutics has major attractions compared with the oral route of administration as (i) it avoids first-pass liver metabolism of the drug, (ii) circumvents exposure of the drug to the chemical rigors of the gastrointestinal ("GI") tract, (iii) may permit delivery of drugs with short biological half-lives and/or narrow therapeutic windows, (iv) may reduce adverse events in patients such as GI distress, (v) may offer more uniform plasma dosing of the drug, (vi) allows prompt interruption of dosing, and (vi) may increase patient compliance.

Active transdermal delivery routes, in which an external stimulus is applied to drive the drug through the barrier, include iontophoresis, sonophoresis, electroporation, microneedles, and application of high velocity solid particles [1] or liquids [2,3] (see [4]). These all require the application of a physical device, with irritation and compliance often an issue. A passive delivery route, in which a formulation containing the drug needs simply to be applied to the skin is substantially preferred. The prime requirements, in general, for a passive transdermal route are (I) that sufficient skin permeation can be achieved, (ii) that skin irritation and skin sensitization be avoided, and (ii) that reasonable delivery efficiency be accomplished.

Only a small number of drugs have been approved for application in transdermal patches (including scopolamine, nitroglycerin, clonidine, estradiol, nicotine, fentanyl, testosterone, norelgestromin with ethinyl estradiol). These share the three characteristics of (I) low molecular mass (<500 Da) [5], (ii) high lipophilicity, and (iii) small required dose (up to milligrams) [4].

Passive approaches for transdermal delivery of drugs based on vesicles, such as liposomes, have shown some promise for other classes of molecules [6-9]. However, these technologies have yet to appear in an FDA-approved transdermal patch product despite more than 20 years of work on vesicle-based formulations.

More than 300 chemical penetration enhancers ("CPEs") have been considered in the literature [10]; [11] although few are useful in a practical sense—many do not provide a significant enhancement of transdermal drug permeation, and most cause skin irritation or present other safety issues. However, Karande et al. have discovered recently that rare combinations of CPEs, called SCOPE formulations, can cause pronounced permeability enhancement, yet little or no skin irritation [12]. A handful of SCOPE formulations were found amongst 5,040 binary CPE combinations. With more than 300 individual CPE's to consider, however, the space of binary and higher combinations is vast, so that very efficient methods for screening how CPE combinations affect skin barrier properties are desirable.

Transdermal delivery also has potential as a route for the delivery of proteins [13] and of genes into the body [12]. In order to develop chemical agents that are effective at promoting the permeation through skin of proteins or of deoxyribonucleic acid ("DNA") or ribonucleic acid ("RNA"), what is again desirable are efficient experimental means of screening large numbers of combinations of such agents and many different packagings of the proteins or nucleic acids, for their effectiveness at achieving effective transport.

Delivery into the Skin: For dermatological indications and for cosmetic applications it may be desirable to delivery an active agent into the skin, but to avoid, if possible, passage into the serum. Local anesthetics [14] are a similar example. The skin is rich in antigen presenting cells, such as the Langerhans cells, so that a dermal Immunization route can be effective, although today required by needle or a jet injector, with the attendant issues of localized soreness, erythema, and hematoma at the injection site.

Avoidance of Penetration into or through the Skin: With wash, rinse and cleanser products, amongst, others, it is desirable that barrier properties of the skin not be impaired, to avoid ingress of potentially harmful agents. Cosmetic benefits from lipid formulations claimed to restore skin barrier have been reported [15].

Modification of Other Skin Barrier Properties: In several classes of medical devices electrical signals are sampled via surface mounted electrodes, such as in electrocardiography or external sphincter electromyography, for which modification of the skin electrical properties is desirable.

Altering the Sensory Properties of Skin: Many classes of personal care products, that include cosmetics, lotions, salves, creams, moisturizers, exfoliants, cleansers or colorants, improve the health, the feel or the appearance of skin.

Emollients, which soften skin, and moisturizers, which add moisture, are used to correct dryness and scaling of the skin. Dry skin results from loss of water from the stratum corneum, causing it to lose its flexibility and become cracked and scaly. The stratum corneum contains natural water-holding substances that retain water seeping out from the deeper layers of the skin. Water is also retained in the stratum corneum by a surface film of natural oil (sebum) and broken-down skin cells, which hinder trans-epidermal water loss ("TEWL") through evaporation. Moisturizers and emollients can function through one or both of two actions [16]. Occlusives provide a layer of oil on the surface of the skin that slows water loss and thus increases the moisture content of the stratum corneum. Humectants are substances, exemplified by glycerin, urea or alpha hydroxy adds [17] such as lactic add or glycolic add, that, when introduced into the stratum corneum, increase its water holding capacity.

An exfoliant, or peeling agent, acts to slough away dead epidermal skin cells and encourage accelerated cell renewal, thus promoting soft and smooth skin that has visual appeal. Exfoliants function by promoting thinning of the stratum corneum through a descaling or keratolytic action.

To develop formulations that are effective as moisturizers, emollients or exfoliants, to assess the impact on skin of other topical applications such as cosmetics, sun screens, salves and cleansers, and to evaluate the biological impact of prospective active Ingredients in cosmetics, as in cosmeceuticals, what is needed is an efficient experimental means of screening large numbers of such formulations for their ability to do one or more of: (i) adsorb to the outer skin surface, (ii) be absorbed into the stratum corneum or other skin layers, (iii) permeate through the stratum corneum, (iv) permeate through the other skin layers and into the vasculature.

Skin Permeation Studies

The traditional method of performing skin permeation studies, including of topical and transdermal drug delivery formulations as well as of ophthalmics, cosmetics, skin care products and pesticides, employs a vertical diffusion cell, first described by T. Franz [18]. Permeation of a chemical agent from an upper donor well, through a skin sample, into a lower receptor well is assessed, under steady state conditions, through analysis of the concentration of chemical agent in the donor and receptor wells, such as by high performance liquid chromatography ("HPLC"). A single Franz diffusion cell can typically perform about one test per square inch of skin per day. While an automated Franz diffusion cell—HPLC system with 6 cells is now available from Logan Instruments Corporation of Somerset, N.J. (www.loganinstruments.com), use of a Franz cell requires (i) a relatively large area of skin, (ii) a substantial equilibration time, and (iii) substantial manual handling.

Discrete designs different from the Franz diffusion cell have also been disclosed, including Bronaugh's Flow Through Diffusion cell [19,20] and Moody's AIVDA system [21]; these also operate on the same principle of steady-state flux measurements. Despite their claimed advantages over Franz diffusion cells, however, their efficiency in screening enhancers is similar to that with Franz diffusion cells.

A related device used to measure the flow of metabolites across a membrane is the Ussing chamber, originally developed to measure the passage of water and sodium ions across short-circuited, isolated frog skin. Like the Franz diffusion cell, the Ussing Chamber consists of an upper donor chamber and a lower receptor chamber, with passage of a chemical agent through the membrane that separates the chambers being measured by analysis of the receptor well contents as described in a paper by Ussing [22], which is incorporated herein by reference. It differs, though, in being equipped to circulate and aerate the buffer solutions on donor and receptor sides, and to measure also the electrical potential across the membrane. Individual Ussing chambers are available, for example, from World Precision Instruments, of Sarasota, Fla. (www.wplinc.com). A 6-fold Ussing chamber arrangement is available from Dipl.-Ing. K. Mussler Scientific Instruments, of Aachen, Germany (www.kmsci.de). Ussing chambers or modified Ussing chambers (e.g. [23]) have been used extensively to measure ion and metabolite transport across many types of membrane but, like the Franz diffusion cell, the Ussing chamber is unsuitable for use in high throughput screening.

An alternative to these discrete cell designs is to use an array format. Thus, U.S. Pat. No. 5,490,415 [24], which is incorporated herein by reference, describes an apparatus used to test diffusion of a drug through a test membrane in which a number of open-top receptor vessels addresses a test membrane captured between this receptor vessel array and a mirror-image donor vessel array. The drug diffuses from a given donor well through the test membrane and into a receptor liquid in the corresponding receptor well. Samples of the receptor liquid might then be transferred using a programmed liquid transfer system, perhaps for assay by a scintillation counter. U.S. Pat. No. 6,043,027 [25], which is incorporated herein by reference, describes testing devices, systems, and methods for evaluating the permeation of various chemicals through different types of cells. One such device is described to comprise a base member and a top member having a plurality of wells which are aligned when the top member is secured to the base member. A membrane sheet which includes at least one layer of cells grown on the sheet is placed between the base member and the top member prior to assembly. Test samples are placed into the wells in the top member and samples are removed from the top and bottom wells at a later time and tested to determine the amount of test sample which permeated through the cells [25].

Still more recently, WO 02/06518 A1 [26], which is incorporated herein by reference, claims an apparatus for measuring transfer of components across a tissue, comprising a support plate; an array of samples supported by the support plate; a tissue specimen overlaying the array of samples; and a reservoir plate secured to a side of the tissue specimen opposite the array of samples, the reservoir plate having an array of reservoirs [26]. Cima et al. recognized the need for a suitable means to fill donor and/or receptor wells. WO 02/06518 A1 [26] claims a feed canula, having a sample feed source and an air evacuation space, which punctures a rubber septum which covers one side of a donor well. By placing the tip of the canula on the tissue it is claimed that air in the donor well will be forced out of the donor well into the air evacuation space, eliminating any air pockets adjacent to the tissue. It is claimed that the tip of the canula can be progressively retracted toward the septum as donor well filling proceeds (as otherwise the air evacuation space will fill with donor well contents). However, this method requires contact of the sharp tip of the canula with the tissue, potentially causing damage to the barrier layers on the top of the tissue. Further, without sophisticated methods it is difficult both to determine to precisely what depth the canula must be inserted (leading to the possibility of severe tissue barrier damage and, minimally, to uncertainty in each case whether or not such damage has occurred), and the extent to which well filling has progressed (making concerted retraction of the canula difficult to control). Further, this 'from near the bottom Introduction' method is not effective in practice at eliminating bubbles, particularly for viscous samples. Additionally, this approach is not claimed to be useful in achieving complete filling of a well compartment.

What was termed a combinatorial method for rapid screening of drug delivery formulations has been disclosed in works by Mitragotri et al. [27] and Karande et al. [28], both of which are incorporated herein by reference. One embodiment of the system described by Mitragotri uses of an array of wells, each potentially containing a different formulation, applied to a single piece of skin, with permeation being monitored via quantitative changes in the single point conductivity of the stratum corneum in the vicinity of each well. Skin conductivity measurements provide a rapid assay to determine the effect of enhancers on skin permeability [28]. The conductivity measurements may be calibrated by comparison with direct permeation measurements, either in the same experimental set-up or in Franz diffusion cells operated under similar conditions [28].

Systems providing parallel diffusion cells have the potential to provide significant gains in the speed with which permeation measurements can be made. However, in general, techniques have not yet been developed for such approaches that (i) are suitable for making measurements at short contact times between skin and formulations (ii) provide automation-friendly methods for ensuring contact of donor and receptor fluids with skin by avoiding the presence of bubbles (iii) allow for partial or complete inversion of the apparatus, and (iv) provide support measurements of skin properties other than permeation.

Unmet Needs

To be able to efficiently asses the effect on the barrier properties of a membrane of a test formulation, suitable for application in high throughput, there is a need for methods and apparatus that would desirably have the following characteristics:

(1) be able to accommodate measurements on skin, as well as on a broad range of other natural and synthetic membranes;
(2) require minimal amount of membrane material and reagents per measurement;
(3) support direct measurements of the permeation, preferably of molecular and particulate entities;
(4) accommodate a range of formulation types, encompassing aqueous or non-aqueous solutions, emulsions and hydrocarbon-based lotions, formulations that might be rubbed onto the skin, and formulations with a volatile component that will evaporate.
(5) be compatible with automation, robotics, experiment and data management systems and suitable for integration into a high throughput experimentation workflow;
(6) support both direct and indirect measurements of the electrical response of the stratum corneum, over a range of times of contact of the test formulation(s) with the membrane, from less than a minute to many hours, and with the possibility of first measurements being accumulated within a few seconds of first test formulation contact;
(7) support measurements of each absorption, that is the degree to which a molecule or material is taken up by the stratum corneum, but without permeation into or through the epidermis, adsorption, that is the adherence of molecular or other entities to the skin exterior, and exfoliation, that is the extent of sloughing off of material from the stratum corneum;

SUMMARY OF THE INVENTION

The present invention provides apparatuses and methods for screening, in high throughput, the effect of test formulations on the barrier properties of a membrane. In a preferred embodiment of the invention the membrane is skin. In an embodiment of the present invention the apparatus and methods enable more efficient measurements of skin permeabilization. Methods and devices are also provided that allow the permeation of molecular or particulate entities through skin to be measured, and of the absorption and adsorption by skin of ingredients in fluid formulations. In yet another embodiment of the invention methods and devices for measuring exfoliation of material from the exterior of the stratum corneum are provided. The apparatuses and methods may be implemented in an array format based on a set of donor vessels, an interleaving piece or pieces of membrane, and a set of receptor vessels. Other embodiments of the methods and devices allow test formulations to be prepared, and for all donor wells to be loaded before contact by the formulation with the membrane is made, and for this contact to then be initiated for all donor wells in a substantially simultaneous fashion. Further methods and devices are disclosed that ensure continued donor and/or receptor fluid contact with the membrane, independent of the orientation of the membrane, as well as providing for the abstraction of samples from the donor well for chemical analysis. Further methods and apparatus are disclosed for preventing cross-talk between adjacent wells, as well as providing for the removal of gas bubbles or of fluid for analysis. In other embodiments of the invention the donor wells may be provided with electrodes, allowing the response of the membrane to applied electrical signals to be monitored.

The invention teaches methods and membrane for the depth-profiling of formulation constituents through the skin, of stratum corneum component disruption, and of loss of material from the stratum corneum through exfoliation.

The present invention provides several substantial advantages, including (i) experiments can be performed with the membrane in a horizontal geometry, but with the donor cells beneath the membrane, (ii) samples can be added or removed from the donor wells during experiments, allowing dynamic measurements of various types to be performed, and (iii) electrical measurements can be made, separately, in all of the wells in a timescale of seconds or less. The present invention also provides other devices and methods such use of a donor plate with a straight-through which, in a donor-cell-uppermost configuration, support measurements of adsorption or exfoliation. The receptor wells are also provided in one of several formats including (i) as a single bath, but provided with posts that provide mechanical support for the membrane, and (ii) as an array of receptor wells which mirrors in array layout that of the donor vessel array. The receptor wells can be filled with fluids, for example, phosphate buffer solution ("PBS"), in the same manner in which the donor wells are filled and each can be equipped with the aforementioned device for ensuring fluid contact with the skin irrespective of the orientation of the device as a whole. The device can be mounted within the space that is addressed by a fluid dispensing and aspirating robot. Measurements of dermal cell viability, through color development or fluorescence can therefore be automated.

The invention thus provides simple, robust and scalable means of performing, in high throughput, studies of the intra- or trans-membrane delivery, absorption, adsorption and irritation, of active components of various types, such as small or large molecule drugs, peptides and proteins, DNA, and constituents of personal care products, such as, moisturizers and exfoliants. The invention also supports screening of the effect of a test formulation on membrane electrical response.

BRIEF DESCRIPTION OF THE DRAWINGS

FIG. 2. Schematic diagrams of circuit wiring plate-donor well plate-lamina-receptor well plate assembly arrangements.

FIG. 5. Schematic diagram of an embodiment of a circuit wiring plate-donor well plate-lamina-receptor well plate assembly, with device for ensuring complete receptor well filling, illustrating certain features.

FIG. 7. Schematic diagrams of an embodiment of a donor well plate-lamina-receptor well plate assembly, with device in the form of a plate for ensuring complete receptor and donor well filling.

FIG. 8. Schematic diagrams of an embodiment of a receptor well array, with duckbill devices that ensure complete receptor well filling, and provide for partial removal of receptor well contents.

FIG. 9. Schematic diagrams of further devices beneficially applied to donor or receptor wells to achieve complete well filling while avoiding the formation of bubbles or air pockets.

FIG. 10. Schematic diagrams of embodiments of a donor well plate-lamina-receptor well plate assemblies, incorporating electrode arrays.

FIG. 11. Schematic diagrams of two forms of apparatus suitable for performing layer-by-layer removal of material from lamina.

DETAILED DESCRIPTION OF THE INVENTION

Figure 1:
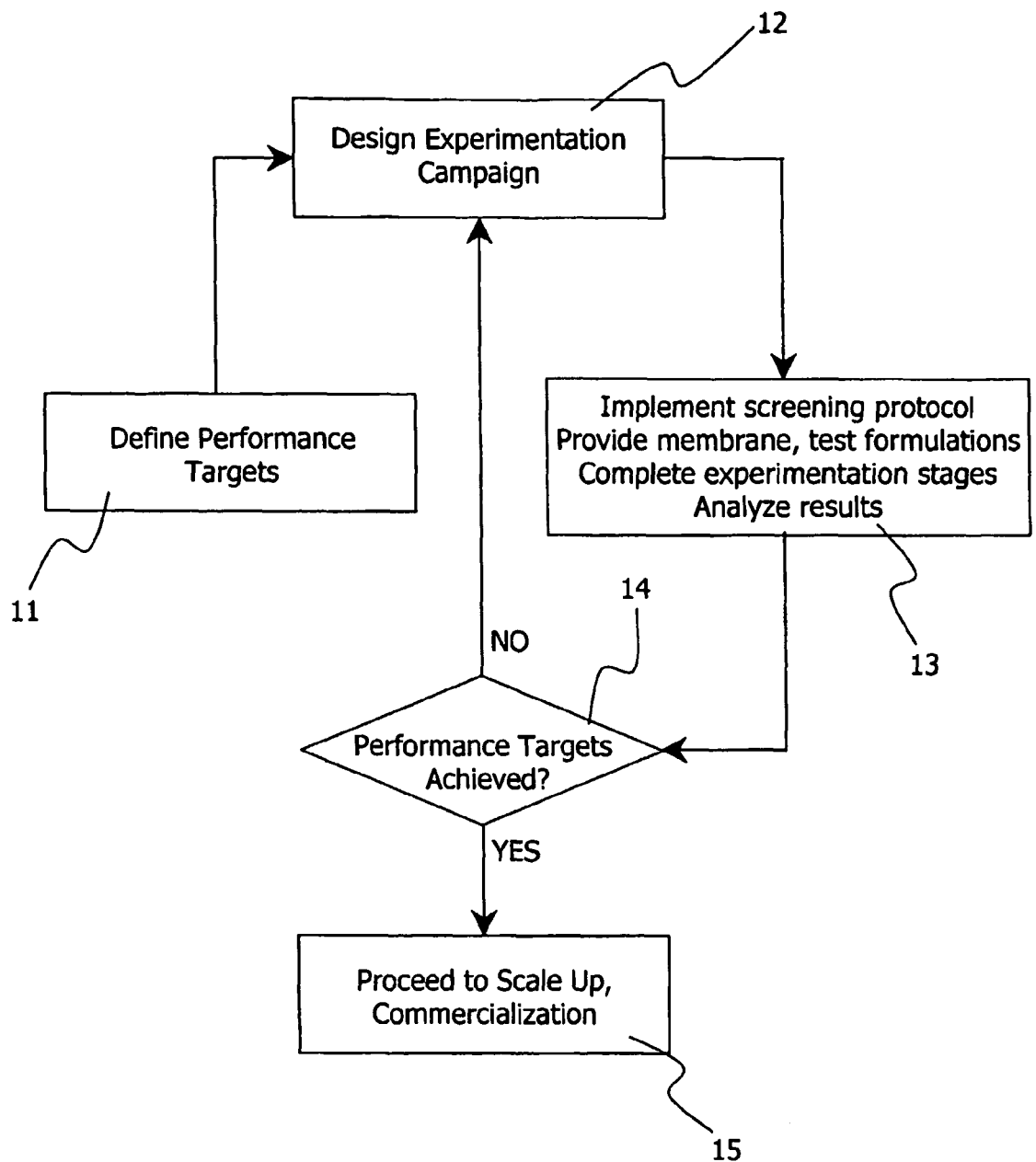
FIG. 1. A schematic of an exemplary workflow followed to realize benefit from the present method and devices.

The present invention relates to high throughput systems and methods that improve the efficiency and speed by which formulations suitable for applying active ingredients to tissues, into tissues or through tissues can be discovered, developed and optimized. The systems and methods are suitable for developing formulations suitable for trans-tissue transfer of active compounds, such as pharmaceuticals or drugs, other compounds, or compound combinations. In one embodiment, the systems and methods may be used to identify the optimal components, such as solvents, carriers, transport enhancers, adhesives, additives, and other excipients, for pharmaceutical formulations that are delivered to a patient via tissue transport, including without limitation, pharmaceutical compositions or formulations administered or delivered transdermally (e.g., in the form of a transdermal delivery device), topically (e.g., in the form of ointments, lotions, gels, and solutions), and ocularly (e.g., in the form of a solution). In another embodiment, the systems and methods may be used to identify the optimal components in topically applied skin moisturizers, anti-aging creams, sun screens and other personal care products

DEFINITIONS AND TERMINOLOGY

The following terms have the following meanings when used herein and in the appended claims. Terms not specifically defined herein have their art recognized meaning.

"Active component" means a substance or compound that imparts a primary utility to a composition or formulation when the composition or formulation is used for its intended purpose. Examples of active components include pharmaceuticals, vitamins, ultra violet ("UV") radiation absorbers, cosmeceuticals, alternative medicines, skin care actives, and nutraceuticals. Active components can be small molecules, proteins or peptides, genetic material, such as DNA or RNA, diagnostic or sensory compounds, agrochemicals, the active component of a consumer product formulation, or the active component of an industrial product formulation.

"adhesive" means a substance that may be used to affix an object to another object. Adhesives may use to attach a device, such as a patch, to a tissue, such as skin. The adhesive may form the matrix of such a patch in which an active component is dissolved or dispersed. The compatibility of the active component with an adhesive is influenced by its solubility in that adhesive; a high solubility is desired in the adhesive to increase the driving force for permeation through the tissue and to improve the stability of the device. Classes of polymers used as adhesives include polyisobutylene, silicone, and acrylic adhesives.

"array" or "sample array" means a plurality of samples associated under a common experiment, or the physical arrangement of a plurality of vessels used to contain samples in a given experiment.

"automated" or "automatically" refers to the use of non-human means such as computer software and robotics. Tasks such as, for example, dispensing, weighing, moving, adding, mixing or analyzing the samples, components, and specimens may be achieved by automated means.

"body surface" refers to skin or mucosal tissue.

"carriers" or equivalently "vehicles" as used herein refer to carrier materials suitable for topical or transdermal drug administration. Carriers and vehicles useful herein include any such material known in the art that is generally non-toxic and does not interact with other components of the composition in a deleterious or unwanted manner. Vehicles may contain one or more excipients and may also contain one or more chemical penetration enhancers. Carriers and vehicles can be, for example, semi-solids, liquids, solvents, solutions, gels, foams, pastes, ointments, triturates, suspensions, or emulsions.

"component" means any substance or compound. A component can be active or inactive.

"creams" means generally viscous liquids or semisolid emulsions, usually either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

"excipient" refers to inactive substances used to formulate pharmaceuticals as a result of processing or manufacture or used by those of skill in the art to formulate pharmaceuticals, alternative medicines, cosmeceuticals, cosmetics, personal care products, dietary supplements, and nutraceuticals for administration to animals or humans.

Preferably, excipients are approved for or considered to be safe for human and animal administration. Examples of suitable excipients include, but are not limited to, acidulents, such as lactic acid, hydrochloric acid, and tartaric acid; solubilizing components, such as non-ionic cationic, and anionic surfactants; absorbents, such as bentonite, cellulose, and kaolin; alkalizing components, such as diethanolamine, potassium citrate, and sodium bicarbonate; anticaking components, such as calcium phosphate tribasic, magnesium trisilicate, and talc; antimicrobial components, such as benzoic acid, sorbic acid, benzyl alcohol, benzethonium chloride, bronopol, alkyl parabens, cetrimide, phenol, phenylmercuric acetate, thimerosol, and phenoxyethanol; antioxidants, such as ascorbic acid, alpha tocopherol, propyl gallate, and sodium metabisulfite; binders, such as acacia, alginic acid, carboxymethyl cellulose, hydroxyethyl cellulose; dextrin, gelatin, guar gum, magnesium aluminum silicate, maltodextrin, povidone, starch, vegetable oil, and zein; buffering components, such as sodium phosphate, malic acid, and potassium citrate; chelating components, such as EDTA, malic acid, and maltol; coating components, such as adjunct sugar, cetyl alcohol, poly-vinyl alcohol, carnauba wax, lactose maltitol, titanium dioxide; controlled release vehicles, such as microcrystalline wax, white wax, and yellow wax; desiccants, such as calcium sulfate; detergents, such as sodium lauryl sulfate; diluents, such as calcium phosphate, sorbitol, starch, talc, lactitol, polymethacrylates, sodium chloride, and glyceryl palmitostearate; disintegrants, such as colloidal silicon dioxide, croscarmellose sodium, magnesium aluminum silicate, potassium polacrilin, and sodium starch glycolate; dispersing components, such as poloxamer 386, and polyoxyethylene fatty esters (polysorbates); emollients, such as cetearyl alcohol, lanolin, mineral oil, petrolatum, cholesterol, isopropyl myristate, and lecithin; emulsifying components, such as anionic emulsifying wax, monoethanolamine, and medium chain triglycerides; flavoring components, such as ethyl maltol, ethyl vanillin, fumaric acid, malic acid, maltol, and menthol; humectants, such as glycerin, propylene glycol, sorbitol, and triacetin; lubricants, such as calcium stearate, canola oil, glyceryl palmitosterate, magnesium oxide, poloxymer, sodium benzoate, stearic acid, and zinc stearate; solvents, such as alcohols, benzyl phenylformate, vegetable oils, diethyl phthalate, ethyl oleate, glycerol, glycofurol, polyethylene glycol, tartazine, triacetin; stabilizing components, such as cyclodextrins, albumin, xanthan gum; and tonicity components, such as glycerol, dextrose, potassium chloride, and sodium chloride; and mixtures thereof. Excipients include those that alter the rate of absorption, bioavailability, or other pharmacokinetic properties of pharmaceuticals, dietary supplements, alternative medicines, or nutraceuticals. Other examples of suitable excipients, such as binders and fillers are listed in Remington's Pharmaceutical Sciences, 18th Edition, Ed. Alfonso Gennaro, Mack Publishing Co. Easton, Pa., 1995 and Handbook of Pharmaceutical Excipients, 3rd Edition, Ed. Arthur H. Kibbe, American Pharmaceutical Association, Washington D.C. 2000, both of which are Incorporated herein by reference. Excipients that are typically used in the formation of transdermal delivery devices, and therefore particularly useful for formulation of the samples of the present invention, are penetration enhancers, adhesives and solvents.

"gels" means, generally semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules", i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

"high throughput" refers to the number of samples generated or screened in a given time period as described herein, typically at least 10, more typically at least 50 to 100, and preferably more than 1000 samples. The high throughput experimentation methods of the present invention can be performed using various forms of samples. Typically, the methods are performed with samples that are either in liquid form in solid form.

"inactive component" means a component that is useful or potentially useful to serve in a composition or formulation for administration of an active component, but does not significantly share in the active properties of the active component or give rise to the primary utility for the composition or formulation. Examples of suitable inactive components include, but are not limited to, enhancers, excipients, carriers, binders, solvents, diluents, stabilizers, additives, adhesives, and combinations thereof.

"lamina" or, equivalently, "test membrane" means a piece of membrane or a sheet of tissue, the interaction of samples with which is tested in the present invention. A lamina may be of natural or synthetic materials, or a combination of both. Examples of suitable types of natural tissue suitable for use as the lamina include, but are not limited to, skin, lung, tracheal, nasal, placental, vaginal, rectal, colon, gut, stomach, bladder, or corneal tissue. Preferably, stratum corneum or skin tissue, such as hairless mouse skin, porcine skin, guinea pig skin, or human skin is used. If human cadaver skin is to be used, one known method of preparing the tissue specimen entails heat stripping by keeping it in water at 60° C. for two minutes followed by the removal of the epidermis, and storage at 4° C. in a humidified chamber; a piece of epidermis is taken out from the humidified chamber prior to the experiments and optionally be supported by a porous support such as Nylon mesh (available from Sefar America Inc. (Tetko Inc.) of Depew, N.Y.; www.seframerica.com, or Fisher Scientific of Pittsburgh, Pa.; www.fishersci.com) to avoid any damage and to mimic the fact that the skin in vivo is supported by mechanically strong dermis. Other types of natural tissues may also be used for the lamina, including living tissue explants, any of a number of endothelial or epithelial cell culture barriers, such as those described in Audus, et al. [29], animal tissue (e.g. rodent, bovine or swine) or engineered tissue-equivalents. Examples of suitable engineered tissues include DERMAGRAFT®, a human fibroblast-derived dermal substitute (available from Smith & Nephew, Inc. of Largo Fla.; www.dermagraft.com), and EpiDerm™ a skin model from human-derived epidermal keratinocytes available from MatTek Corporation, Ashland, Mass. (www.mattek.com), and those taught in U.S. Pat. No. 5,266,480 [30], which is incorporated herein by reference. A synthetic membrane, such as an elastomeric membrane, may also be used. The material of the lamina may be freestanding, or may be supported on a substrate. The membrane or tissue used as the lamina is chosen based on the desired application. Screening of formulations for transdermal delivery is preferably conducted using pigskin; to screen formulations for oral drug delivery mucosal membrane might be used, and so forth.

"library" means a plurality of samples.

"liquid form" means that the sample containing the component or components being measured or analyzed is in the form of a liquid, which includes, without limitation, liquids, solutions, emulsions, suspensions, and any of the foregoing having solid particulates dispersed therein.

"lotions" which are typically preferred for delivery of cosmetic agents, are preparations to be applied to the skin surface with low friction, and are typically liquid or semi-liquid preparations in which solid particles, including the active agent, are present in a water or alcohol base. Lotions are usually suspensions of solids. Lotions are preferred formulations for treating large body areas, because of the ease of applying a more fluid composition. In general the insoluble matter in a lotion is finely divided. Lotions will typically contain suspending agents to produce better dispersions as well as compounds useful for localizing and holding the active agent in contact with the skin, e.g., methylcellulose, sodium carboxymethylcellulose, or the like.

"mucosa" means a mucous membrane that covers the inside of a hollow organ such as the membranes covering the oral cavity, the nasal cavity, the rectum and the vagina.

"ointments" means semisolid preparations that typically may be based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should preferably be inert, stable, nonirritating and nonsensitizing. As explained in Remington: The Science and Practice of Pharmacy, 19th Edition [31] ointment bases may be grouped in four classes: oleaginous bases; emulsifiable bases; emulsion bases; and water-soluble bases [31]. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil ("w/o") emulsions or oil-in-water ("o/w") emulsions, and include, for example, cetyl alcohol, glyceryl monostearate, lanolin and stearic acid.

"paste" means semisolid dosage forms in which the active agent is suspended in a suitable base. Depending on the nature of the base, pastes are often divided between fatty pastes or those made from a single-phase aqueous gel. The base in a fatty paste is generally petrolatum or hydrophilic petrolatum or the like. The pastes made from single-phase aqueous gels generally incorporate carboxymethylcellulose or the like as a base.

"penetration enhancement" means a measure of the degree to which a test formulation is successful in increasing the permeability of a lamina such as a test membrane skin or mucosa.

"permeation enhancer" or, equivalently, "penetration enhancer", "chemical penetration enhancer" or "CPE" means a substance used to modify, usually to increase, the rate of permeation through a lamina, such as skin or other tissue of one or more products in a formulation, and includes all such substances now known or later developed or discovered. See Santus et al. [10] and Williams [11]. Various enhancers are listed below. These enhancers are compiled from over 350 references and have been classified into several categories and subcategories based on their structure or their effect on permeability:

Surfactants: These are amphiphilic molecules with a hydrophilic head and a hydrophobic tail group. The tail length and the chemistry of the head group play an important role in determining their effect on skin permeability. Surfactants can be categorized into four groups, cationic, anionic, non-ionic, and zwitterionic depending on the charge on the head group. Prominent examples of surfactants that have been used for transdermal delivery include: Brij (various chain lengths), HCO-60 surfactant, Hydroxypolyethoxydodecane, Lauryl sarcosine, Nonionic surface active agents, Nonoxynol, Octoxynol, Phenylsulfonate, Pluronic, Polyoteates (nonionic surfactants) Rewopal HV10, Sodium laurate, Sodium oleate, Sorbitan dilaurate, Sorbitan dioleate, Sorbitan monolaurate, Sorbitan monooleates, Sorbitan trilaurate, Sorbitan trioleate, Span 20, Span 40, Span 85, Synperonic NP, Triton X-100, Tweens, Sodium alkyl sulfates, and alkyl ammonium halides.

Azone and related compounds: These compounds are also amphiphilic and possess a nitrogen molecule in their head group (preferably in the ring). The presence of a nitrogen atom in a ring creates a bulky polar head group with the potential for strong disruption of stratum corneum. Examples of such compounds include N-Acyl-hexahydro-2-oxo-1H-azepines, N-Alkyl-dihydro-1,4-oxazepine-5,7-diones, N-Alkylmorpholine-2,3-diones, N-Alkylmorpholine-3,5-diones, Azacycloalkane derivatives (-ketone,-thione), Azacycloalkenone derivatives, 1-[2-(Decylthio)ethyl]azacyclopentan-2-one (HPE-101), N-(2,2), Dihydroxyethyl) dodecylamine, 1-Dodecanoylhexahydro-1-H-azepine, 1-Dodecyl azacycloheptan-2-one (azone or laurocapram), N-Dodecyl diethanolamine, N-Dodecyl-hexahydro-2-thio-1H-azepine, N-Dodecyl-N-(2-methoxyethyl)acetamide, N-Dodecyl-N-(2-methoxyethyl)isobutyramide, N-Dodecyl-piperidine-2-thione, N-Dodecyl-2-piperidinone, N-Dodecyl pyrrolidine-3,5-dione N-Dodecyl pyrrolidine-2-thione, N-Dodecyl-2-pyrrolidone, 1-Farnesytazacycloheptan-2-one, 1-Farnesylazacyclopentan-2-one, 1-Geranyl azacycloheptan-2-one, 1, Geranylazacyclopentan-2-one, Hexahydro-2-oxo-azepine-1-acetic acid esters, N-(2, Hydroxyethyl)-2-pyrrolidone, 1-Laurylazacycloheptane, 2-(1-Nonyl)-1,3- dioxolane, 1-N-Octylazacyclopentan-2-one, N-(1-oxododecyl)-hexahydro-1H-azepine, N-(1, Oxododecyl)-morpholines, 1-Oxohydrocarbyl-substituted azacyclohexanes, N-(1-Oxotetradecyl)-hexahydro-2-oxo-1H-azepine, N-(1 Thiododecyl)-morpholines.

Solvents and related compounds These molecules are solubility enhancers. Some of them also extract lipids, thereby increasing skin permeability. Examples of solvents include Acetamide and derivatives, Acetone, n-Alkanes (chain length between 7 and 16), Alkanols, diols, short-chain fatty adds, Cydohexyl-1,1-dimethylethanol, Dimethyl acetamide, Dimethyl formamide, Ethanol, Ethanol/d-limonene combination, 2-Ethyl-1,3-hexanediol, Ethoxydiglycol (transcutol), Glycerol, Glycols, Lauryl chloride, Limonene, N-Methylformamide, 2-Phenylethanol, 3-Phenyl-1-propanol, 3-Phenyl-2-propen-1-ol, Polyethylene glycol, Polyoxyethylene sorbitan monoesters, Polypropylene glycol 425, Primary alcohols (tridecanol), Procter & Gamble system: small polar solvent (1,2-propane diol, butanediol, C3-6 triols or their mixtures and a polar lipid compound selected form C16 or C18 monounsaturated alcohol, C16 or C1-8 branched saturated alcohol and their mixtures), Span 20, Squalene, Triacetin, Trichloroethanol, Trifluoroethanol, Trimethylene glycol, Xylene, DMSO and related compounds.

Fatty alcohols, fatty acids, fatty esters, and related structures: These molecules are classic bilayer fluidizers. Examples of these enhancers include Aliphatic alcohols, Decanol, Lauryl alcohol (dodecanol), Unolenyl alcohol, Nerolidol, 1-Nonanol, n-Octanol, Oleyl alcohol, Butyl acetate, Cetyl lactate, Decyl N,N-dimethylamino acetate, Decyl N,N-dimethylamino isopropionate, Diethyleneglycol oleate, Diethyl sebacate, Diethyl succinate, Diisopropyl sebacate, Dodecyl N,N-dimethylamino acetate Dodecyl (N,N-dimethylamino)-butyrate, Dodecyl N,N-dimethylamino isopropionate, Dodecyl 2-(dimethylamino)proplonate, EO-5-oleyl ester, Ethyl acetate, Ethylaceto acetate, Ethyl propionate, Glycerol monoethers, Glycerol monolaurate, Glycerol monooleate, Glycerol monolinoleate, Isopropyl isostearate, Isopropyl linoleate, Isopropyl myristate, Isopropyl myristate/fatty acid monoglyceride combination, Isopropyl myristate/ethanol/L-lactic acid (87:10:3) combination, Isopropyl palmitate, Methyl acetate, Methyl caprate, Methyl laurate, Methyl propionate, Methyl valerate, 1-Monocaproyl glycerol, Monoglycerides (medium chain length), Nicotinic esters (benzyl), Octyl acetate, Octyl N,N-dimethylamino acetate, Oleyl oleate, n-Pentyl N-acetylprolinate, Propylene glycol monolaurate, Sorbitan dilaurate, Sorbitan dioleate, Sorbitan monolaurate, Sorbitan monooleates, Sorbitan trilaurate, Sorbitan trioleate, Sucrose coconut fatty ester mixtures, Sucrose monolaurate, Sucrose monooleate, Tetradecyl N,N-dimethylamino acetate, Alkanoic adds, Capric acid, Diacid, Ethyloctadecanoic add, Hexanoic acid, Lactic acid, Lauric acid, Unoelaidic acid, Linclelc acid, Linolenic acid, Neodecanoic acid, Oleic add, Palmitic acid, Pelargonic acid, Propionic acid, Vaccenic acid, a-Monoglyceryl ether, EO-2-oleyl ether, EO-5-oleyl ether, EO-10-oleyl ether, Ether derivatives of polyglycerols and alcohols (1-O-dodecyl-3-O-methyl-2-O-(29,39-dihydroxypropyl)glycerol), L-α-amino-acids, Lecithin, Phospholipids, Saponin/phospholipids, Sodium deoxycholate, Sodium taurocholate, Sodium tauroglycocholate.

Others: Aliphatic thiols, Alkyl N,N-dialkyl-substituted amino acetates, Anise oil, Anticholinergic agent pretreatment, Ascaridole, Biphasic group derivatives, Bisabolol, Cardamom oil, 1-Carvone, Chenopodium (70% ascaridole), Chenopodium oil, 1,8Cineole (eucalyptol), Cod liver oil (fatty acid extract), 4-Decyloxazolidin-2-one, Dicyclohexyl-methylamine oxide, Diethyl hexadecylphosphonate, Diethyl hexadecylphosphoramidate, N,N-Dimethyl dodecylamine-N-oxide, 4,4-Dimethyl-2-undecyl-2-oxazoline, N-Dodecanoyl-L-amino acid methyl esters, 1,3-Dioxacycloalkanes, (SEPAs), Dithiothreitol, Eucalyptol (cineole), Eucalyptus oil, Eugenol, Herbal extracts, Lactam N-acetic acid esters, N-Hydroxyethalaceamide, 2-Hydroxy-3-oleoyloxy-1-pyroglutamyloxypropane, Menthol, Menthone, Morpholine derivatives, N-Oxide, Nerolidol, Octyl-β-D-(thio)glucopyranosides, Oxazolidinones, piperazine derivatives, Polar lipids, Polydimethylsiloxanes, Poly [2-(methylsulfinyl)ethyl acrylate], Polyrotaxanes, Polyvinylbenzyldimethylalkylammonium chloride, Poly(N-vinyl-N-methyl acetamide), Prodrugs, Saline (skin hydration), Sodium pyroglutaminate, Terpenes and azacyclo ring compounds, Vitamin E (α-tocopherol), Ylang-ylang oil, N-Cyclohexyl-2-pyrrolidone, 1-Butyl-3-dodecyl-2-pyrrolidone, 1,3-Dimethyl-2-imidazolikinone, 1,5Dimethyl-2-pyrrolidone, 4,4-Dimethyl-2-undecyl-2-oxazoline, 1-Ethyl-2-pyrrolidone, 1-Hexyl-4-methyloxycarbonyl-2-pyrrolidone, 1-Hexyl-2-pyrrolidone, 1-(2 Hydroxyethyl)pyrrolidinone, 3-Hydroxy-N-methyl-2-pyrrolidinone, 1-Isopropyl-2-undecyl-2-imidazoline, 1-Lauryl-4-methyloxycarbonyl-2-pyrrolidone, N-Methyl-2-pyrrolidone, Poly(N-vinylpyrrolidone), Pyroglutamic acid esters, Acid phosphatase, Calonase, Orgelase, Papain, Phospholipase A-2, Phospholipase C, Triacylglycerol hydrolase.

"pharmaceutical" or, used interchangeably, "drug" means any substance or compound that has a therapeutic, disease preventive, diagnostic, or prophylactic effect when administered to an animal or a human. The term pharmaceutical includes prescription drugs and over the counter drugs. Pharmaceuticals suitable for use in the invention include all those known or to be developed. Examples of suitable pharmaceuticals include, but are not limited to, cardiovascular pharmaceuticals, such as amlodipine besylate, losartan potassium, irbesartan, diltiazem hydrochloride, clopidogrel bisulfate, digoxin, abciximab, furosemide, amiodarone hydrochloride, beraprost, tocopheryl nicotinate; antiinfective components, such as amoxicillin, davulanate potassium, azithromycin, itraconazole, acyclovir, fluconazole, terbinafine hydrochloride, erythromycin ethylsuccinate, and acetyl sulfisoxazole; psychotherapeutic components, such as sertraline hydrochloride, venlafaxine, bupropion hydrochloride, olanzapine, buspirone hydrochloride, alprazolam, methylphenidate hydrochloride, fluvoxamine maleate, and ergoloid mesylates; gastrointestinal products, such as lansoprazole, ranitidine hydrochloride, famotidine, ondansetron hydrochloride, granisetron hydrochloride, sulfasalazine, and infliximab; respiratory therapies, such as loratadine, fexofenadine hydrochloride, cetirizine hydrochloride, fluticasone propionate, salmeterol xinafoate, and budesonide; cholesterol reducers, such as atorvastatin calcium, lovastatin, bezafibrate, ciprofibrate, and gemfibrozil; cancer and cancer-related therapies, such, as paclitaxel, carboplatin, tamoxifen citrate, docetaxel, epirubicin hydrochloride, leuprolide acetate, bicalutamide, goserelin acetate implant, irinotecan hydrochloride, gemcitabine hydrochloride, and sargramostim; blood modifiers, such as epoetin alfa, enoxaparin sodium, and antihemophilic factor; antiarthritic components, such as celecoxib, nabumetone, misoprostol, and rofecoxib; AIDS and AIDS-related pharmaceuticals, such as lamivudine, indinavir sulfate, stavudine, and lamivudine; diabetes and diabetes-related therapies, such as metformin hydrochloride, troglitazone, and acarbose; biologicals, such as hepatitis B vaccine, and hepatitis A vaccine; hormones, such as estradiol, mycophenolate mofetil, and methylprednisolone; analgesics, such as tramadol hydrochloride, fentanyl, metamizole, ketoprofen, morphine sulfate, lysine acetylsalkylate, ketorolac tromethamine, morphine, loxoprofen sodium, and ibuprofen; dermatological products, such as isotretinoin and clindamycin phosphate; anesthetics, such as propofol, midazolam hydrochloride, and lidocaine hydrochloride; migraine therapies, such as sumatriptan succinate, zolmitriptan, and rizatriptan benzoate; sedatives and hypnotics, such as zolpidem, zolpidem tartrate, triazolam, and hycosine butylbromide; imaging components, such as iohexyl, technetium, TC99M, sestamibi, lomeprol, gadodiamide, ioversol, and lopromide; and diagnostic and contrast components, such as alsactide, americium, betazole, histamine, mannitol, metyrapone, petagastrin, phentolamine, radioactive $B_{12}$, gadodiamide, gadopentetic acid, gadoteridol, and perflubron. Still other examples of suitable pharmaceuticals are listed in 2000 *MedAd News* 19:56-60 and *The Physicians Desk Reference*, 53rd. Edition, pages 792-796, Medical Economics Company (1999), both of which are incorporated herein by reference.

Examples of suitable veterinary pharmaceuticals include, but are not limited to, vaccines, antibiotics, growth enhancing components, and dewormers. Other examples of suitable veterinary pharmaceuticals are listed in *The Merck Veterinary Manual, 8th Edition*, Merck and Co., Inc., Rahway, N.J., 1998; (1997); *The Kirk-Othmer Encyclopedia of Chemical Technology*, Volume 24 Kirk-Othmer (4th Edition at page 826); and *Veterinary Drugs* by A. L. Shore and R. J. Magee, American Cyanamid Co. in *The Encyclopedia of Chemical Technology* 2nd. Edition, Vol. 21, each of which is incorporated herein by reference "reservoir medium" refers to a liquid, solution, gel, or sponge that is chemically compatible with the components in a sample and the lamina being used in an apparatus or method of the present invention. In one embodiment of the present invention, the reservoir medium comprises part of the specimen taken to measure or analyze the transfer, flux, or diffusion of a component across a tissue barrier. Preferably, the reservoir medium is a liquid or solution.

"sample" or equivalently "formulation" means a mixture of a plurality of active components and a plurality of inactive components. A sample typically contains at least one active and at least one inactive, although approximate measurements of penetration enhancement may be made by using a chemical penetration enhancer or a combination of chemical penetration enhancers, usually with a solvent, but without an active component. A sample may contain one active component but can contain multiple active components. Samples and formulations can take many forms, which include, without limitation, solids, semisolids, liquids, solutions, emulsions, suspensions, triturates, gels, films, foams, pastes, ointments, adhesives, highly viscoelastic liquids and any of the foregoing having solid particulates dispersed therein.

When performing high throughput experimentation on samples it is preferred that the samples are placed in an array format. Samples in a sample array may each comprise a different composition, or the sample array may contain replicate samples, standards, also termed, controls, and/or blanks. A sample can be present in any container or holder or in or on any material or surface. Preferably, the samples are located at separate sites. Preferably, where samples are in an array format, samples are contained an array of sample wells, for example, a 24, 36, 48, 96, 384 or 1,536 well plate array. The sample can comprise less than about 100 milligrams of an active component, preferably, less than about 1 milligram, more preferably, less than about 100 micrograms, and even more preferably, less than 100 nanograms. Preferably, the sample has a total volume of about 1-200 µl, more preferably about 5-150 µl, and most preferably about 10-100 µl.

"skin" means the tissue layer forming the external covering of the body of a human, an animal, or another organism which is in turn characterized by a number of sub-layers such as the dermis, the epidermis and the stratum corneum.

"skin care actives" means all compounds or substances now known or later demonstrated to provide benefit when applied to the skin of patients or consumers and all compounds now claimed or in the future claimed to provide benefit when applied to the skin of patients or consumers. Skin care actives may provide benefits, or claimed benefits, in areas such as wrinkle removal or wrinkle reduction, firming of skin, exfoliation of skin, skin lightening, treatment of dandruff, treatment of acne, skin conditioning, development of tans and artificial tans, improvement of skin moisture content, improvement of skin barrier properties, control of sweat, anti-ageing, reduction or avoidance of irritation and reduction or avoidance of inflammation. Skin care actives can be molecules such as protease and/or enzyme inhibitors, anti-coenzymes, chelating agents, antibodies, antimicrobials, humectants, vitamins, skin protectants and/or skin soothing agents, plant extracts and the like. Examples of skin care actives include but are not limited to vitamin C, vitamin E (alpha tocopherol), retinoids, soy derivatives (e.g. isoflavones), green tea polyphenols, alpha hydroxy acids (e.g. glycolic and lactic acid), beta hydroxy acids (e.g. salkylic acid), poly hydroxy acids, alpha lipoic add, hemp oil (glycerides), niacinamide, dimethyl aminoethanol, coenzyme Q10, kinetin (plant growth hormone), dimethyl sulfone and botulinum toxin.

"solid form" means that the sample containing the component or components being measured or analyzed is in the form of a solid or semi-solid, which includes, without limitation, triturates, gels, films, foams, pastes, ointments, adhesives, high viscoelastic liquids, high viscoelastic liquids having solid particulates dispersed therein, and transdermal patches.

"solvent" means a fluid in which a component such as an active component, carrier, or adhesive will dissolve. Solvents are selected based on the solubility of the material to be dissolved, chemical compatibility, biocompatibility and other factors. Aqueous solvents can be used to make matrices formed of water soluble polymers. Organic solvents will typically be used to dissolve hydrophobic and some hydrophilic polymers. Preferred organic solvents are volatile or have a relatively low boiling point or can be removed under vacuum and which are acceptable for administration to humans in trace amounts, such as methylene chloride. Other solvents, such as ethyl acetate, ethanol, methanol, dimethyl formamide (DMF), acetone, acetonitrile, tetrahydrofuran (THF), acetic add, dimethyl sulfoxide (DMSO) and chloroform, and combinations thereof, also may be utilized. Preferred solvents are those rated as class 3 residual solvents by the Food and Drug Administration, as published in the Federal Register vol. 62, number 85, pp. 24301-24309 (May 1997) which is incorporated herein by reference. Solvents for drugs will typically be distilled water, buffered saline, Lactated Ringer's or some other pharmaceutically acceptable carrier.

"transdermal drug delivery" or "transdermal drug administration" refers to administration of a drug to the skin surface of an individual so that the drug passes through the skin tissue and into the individual's blood stream. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

"topical drug delivery", "topical drug administration" or "dermal delivery" is used in its conventional sense to mean delivery of a topical drug of a pharmacologically active agent to the skin or mucosa, as in, for example, the treatment of various skin disorders. Topical drug administration, in contrast to transdermal administration, is often used to provide a local rather than a systemic effect.

Various additives, known to those skilled in the art, may be included in topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, e.g., to inhibit growth of microbes such as yeasts and molds. Suitable antimicrobial agents are typically selected from the group consisting of the methyl and propyl esters of p-hydroxybenzoic acid (e.g., methyl and propyl paraben), sodium benzoate, sorbic acid, imidurea, and combinations thereof.

Overall Description of Workflow

Figure 13:
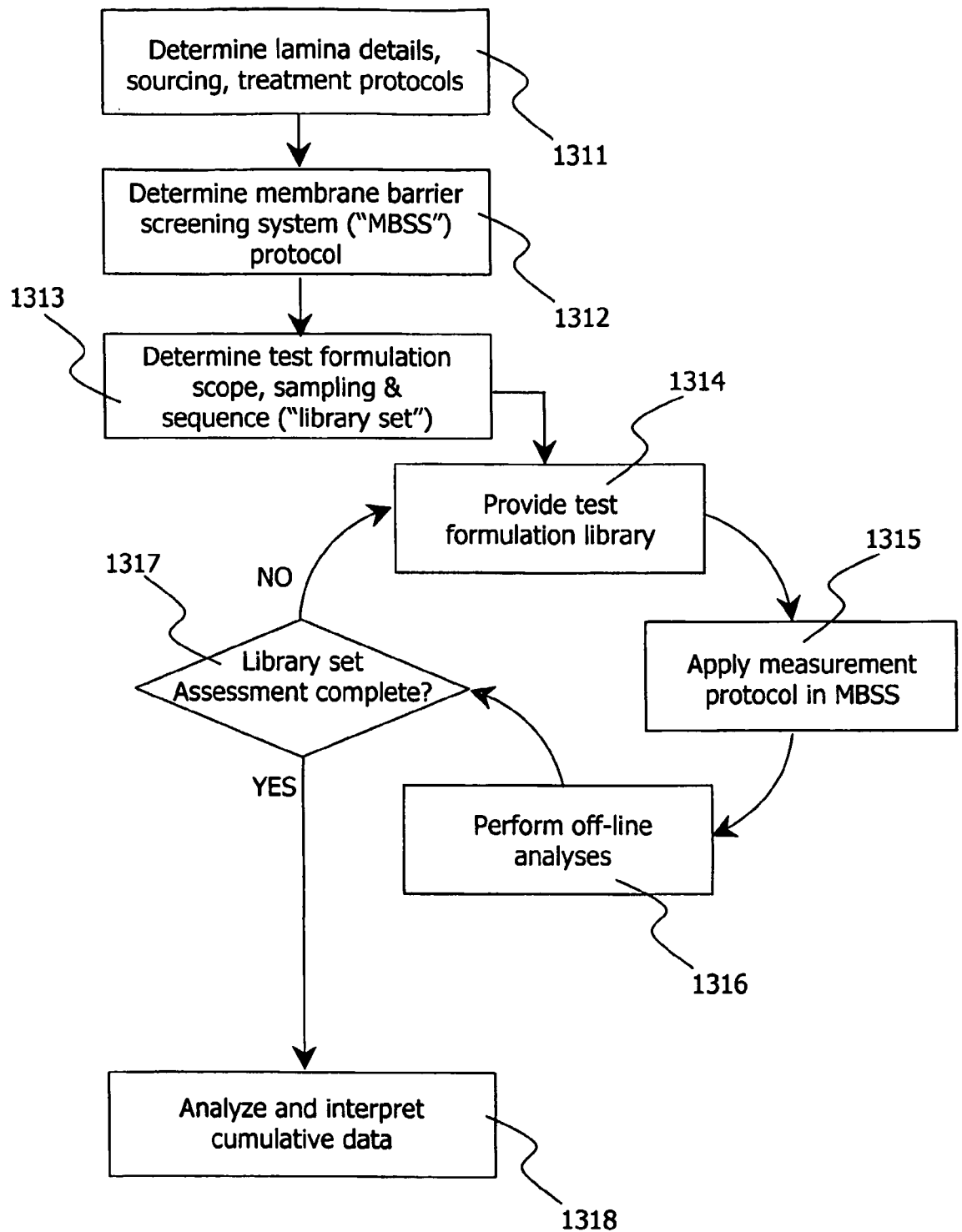
FIG. 13. Schematic diagram of an illustrative workflow executed in completing a program or work according to the present invention.
Figure 14:
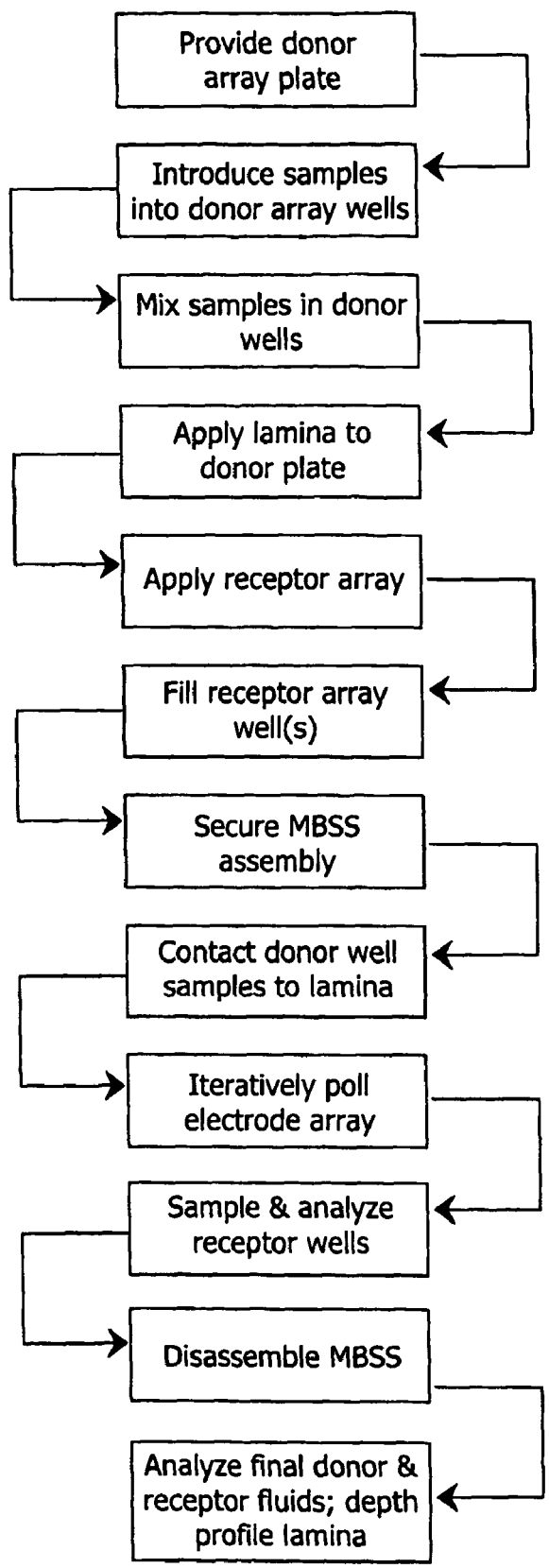
FIG. 14. Schematic diagram of an illustrative workflow executed in completing an experimentation stage, detailing elements of the "apply measurement protocol in membrane barrier screening system (MBSS)" step of FIG. 13.

Referring more specifically to the drawings, for illustrative purposes one embodiment of the present invention is depicted in the methods generally shown in FIG. 1, and FIG. 13 and FIG. 14. It will be appreciated that the methods may vary as to the specific steps and sequence, without departing from the basic concepts as disclosed herein. The steps depicted and/or used in methods herein may be performed in a different order than as depicted and/or stated. The steps are merely exemplary of the order these steps may occur. The steps may occur in any order that is desired, such that it still performs the goals of the claimed invention. All documents including all described or cited herein are expressly incorporated by reference into the disclosure as though set forth in full.

An overall workflow that is beneficially applied is illustrated in FIG. 1. The workflow begins with the definition of a set of performance targets or technical objectives (11). By way of specific example but not limitation, the commercial objective might be to develop a combination of CPE's that is capable of yielding an improvement in the skin permeation rate for a hydrophilic molecule with a molecular weight of 630 Da, that is known to cause beneficial effects when applied to cells in the human dermis, of at least a factor of 50 compared with the permeation rate in the absence of a CPE. Based on the performance targets and whatever prior knowledge on the system are available, a set or series of sets of experiments is designed (12). In the illustrative example, this design stage (12) entails decisions as to what type of skin sample or model to employ in the initial screening; how the initial skin barrier modification screening will be performed; what blanks, controls, and degree of replication will be included; which individual CPE's, which combinations, and which relative and total concentrations will be considered; what acceptance threshold for barrier modification will be used to define "hits"; what subsequent work will be applied to such hits; the operational flow such as the relative placement of equipment applied in the various experimentation operations, which materials will be archived and which discarded etc.; the set up of the software systems that will manage and store the information associated with the various experimentation operations and the various data generated, including how the operational and analytical data will be accumulated, stored and interpreted; and other logistical details, such as time-scheduling of staff and equipment access, safety considerations, degree of supervision required etc. With the experimentation campaign planned, the subsequent stage entails execution of the set(s) of designed experiments, including implementation and validation of the skin barrier screening protocol in the membrane barrier screening system ("MBSS"), provision of the membrane and test formulations, completion of the experimentation stages, and analysis of the experimentation results (13). With completion of this set of experiments, a decision is then made as to whether the performance criteria have been achieved (14), in which case the sample information can be advanced towards a next level of decisions relative to further validation and optimization of hits, and subsequent scale up, perhaps by evaluation on a larger scale, and then commercialization (15). If the performance criteria have not been met, the information gained in the experimentation cycle might be used for a subsequent design process (12), in a next iteration around the experimentation workflow. Iterations may be continued until success is achieved, or until a decision to discontinue is reached.

Description of Apparatus

General layout: FIG. 2 illustrates certain elements of the apparatus, according to two embodiments of the present invention. A lamina (212) is sandwiched between a donor plate (211) and a receptor plate (213). In one embodiment of the invention the lamina may be a contiguous piece of tissue, such as a skin, as shown in the FIG. 2 (212). The lamina may also be provided as a plurality of pieces or strips (223). In one embodiment of the Invention the separate pieces may be formed by making cuts in a larger lamina. Where the lamina is a tissue specimen cuts may be beneficially applied in some embodiments of the invention to prevent lateral diffusion through the tissue specimen between adjacent samples wells or to improve the electrical isolation of adjacent lamina sections.

Any number of methods of cutting the laminar may be employed in embodiments of the invention where lamina pieces are formed by cutting including mechanical scribing or cutting, laser cutting, or crimping. Preferably, laser scribing is used as it avoids mechanical pressure from a cutting tool which can cause distortion and damage to the lamina. Laser cuts may be performed with very small kerfs which permit a relatively high density of samples and more efficient tissue specimen utilization. Laser tools are available that minimize the region that is heated, thereby reducing damage to tissue specimen, as described below.

In one embodiment of the invention the donor plate is provided an array of channels (214) that may have cylindrical or other shape which, sealed on one side by the lamina, form the donor wells. The donor plate may be any rigid grid or plate suitable for containing the samples that has sufficient mechanical rigidity and can support the desired number of channels. For example, the donor plate may be a 24, 36, 48, 72, 96, 384 or 1536 well plate. Preferably, the donor wells have a cylindrical shape with cross sectional diameter between about 0.1 mm to about 50 mm, more preferably about 0.5 mm to about 10 mm, and most preferably about 1 mm to about 7 mm. For example, a 3 mm well diameter format with 6 mm spacing between the wells may be used to make measurements on the order of 7,000 samples for 0.25 $m^2$ of lamina, such as skin. An array can comprise 24, 36, 48, 96, or more samples, preferably at least 1,000 samples, more preferably, at least 10,000 samples.

In some embodiments of the present invention the receptor plate (213) is provided with an array of wells which mirrors that of the donor wells, so that each donor well has a corresponding receptor well, separated from it by the lamina.

FIG. 2 also illustrates elements that may be utilized according to various embodiments of the present inventive apparatus. For example, a circuit wiring plate (216) equipped with an array of electrodes (219) is shown above the donor plate. Preferably, the electrode array geometry is similar to that of the donor plate, so that when the apparatus is fully assembled each of the electrodes in the array (219) can be brought into contact with a sample in the donor well. In another preferred embodiment of the invention the electrodes protrude into the donor well. When the donor well is filled with a fluid, partially or fully, the electrode protruding into that well makes contact with the fluid, causing an electrical connection then to be made to the donor-side surface of the lamina, if the liquid is electrically conducting. In a preferred embodiment the electrode array is constructed from a printed circuit board of suitable size and provides wiring paths from each electrode to the perimeter of the circuit wiring plate (216), from which wiring connections (217) can be made to equipment such as, for example, signal generators and measurement equipment. In a preferred embodiment, the wire from each of the electrodes is terminated into one of the connections of one or more plugs mounted to the circuit wiring plate. The plugs are preferably a standard off-the-shelf component. For an 8×12 96-fold array format, in a particularly preferred embodiment, four RS232 female plugs (each of which supports up to 25 connections) are used for this purpose. Such use of plugs simplifies the making and breaking of connections between the electrodes in the electrode array and the circuitry used in the present invention for accumulating electrical response data. The circuit wiring plate (216) may also be provided with an array of holes (218) through each of which fluid may be introduced or removed, thereby providing a means of adding or abstracting samples from an array of donor wells below the electrode array. In preferred embodiments of the invention a manual pipette or a robot liquid handler is used to introduce or remove samples through the array of holes.

The donor plate is further provided with a set of parallel slots (215) through which a blade (222), preferably a ceramic blade, can be applied to cut the lamina when sandwiched between donor and receptor plates. Cutting the lamina and leaving such a ceramic blade (222) in place may be used to remove possible electrical and permeation paths between a donor well and adjacent donor wells or between a given donor well and receptor wells other than the receptor well immediately opposite the given donor well.

The receptor plate may be provided with a parallel set of grooves (220) arranged in a mirror image fashion to the donor plate parallel slots, so that the ceramic blades that are introduced through the donor plate slits can pass completely through the lamina and into the receptor plate grooves, before further passage is prevented by the bottoms of the grooves in the receptor plate. The receptor plate (213) may also be provided, with a set of parallel slots, arrangement orthogonally to the slits in the donor plate. Through these slots a second set of ceramic blades can be introduced, which can be forced through the lamina, before their passage is prevented by the donor plate, or the tops of grooves in the bottom face of the donor plate. In this fashion the lamina, even while sandwiched between donor and receptor plate, can be sliced from either the donor or receptor plate side to produce strips, or from both sides to produce rectangles or squares of lamina (223), with each piece isolated from its neighbors by the cuts. In a particularly preferred embodiment of the invention the blades are provided with slots, enabling both sets of blades to be left in place after the cutting, as illustrated in the right hand side of FIG. 2B.

It will be appreciated that the specifics of the apparatus may vary from this description, without departing from the basic concepts as disclosed herein.

Figure 3:
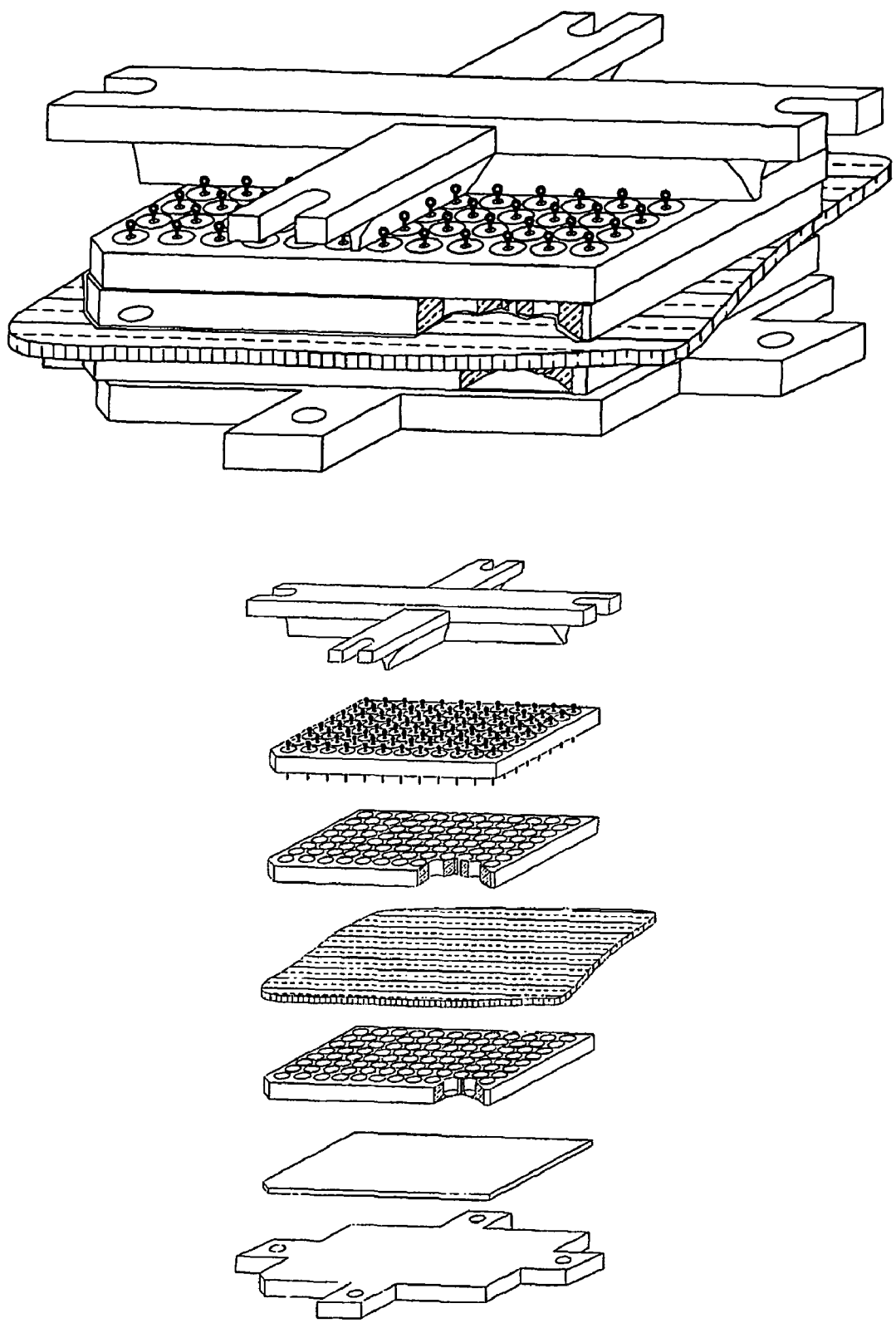
FIG. 3. Schematic diagram of an embodiment of a circuit wiring plate-donor well plate-lamina-receptor well plate assembly, illustrating certain features.
Figure 4:
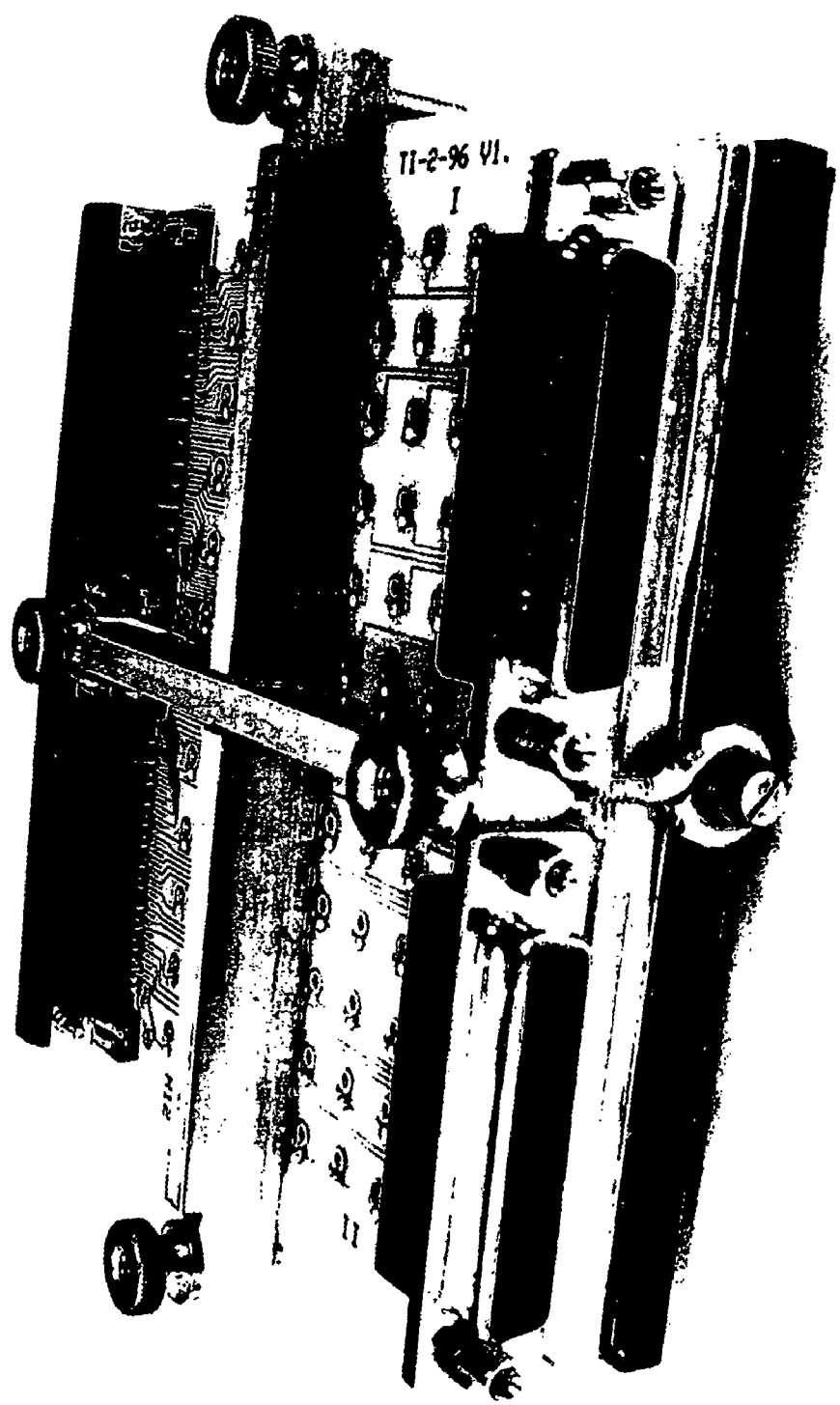
FIG. 4. Photograph of an embodiment of a circuit wiring plate-donor well plate-lamina-receptor well plate assembly, illustrating certain features.

Elements of the present inventive apparatus are further illustrated in FIG. 3 and FIG. 4.

Choice of array format: The array format used with the present invention may be any one of many described previously in the literature. For example, a 24, 36, 48, 96, 384 or 1,536 well plate format such provided in microtitre plates available from Millipore, Bedford, Mass. (www.millipore.com) might be chosen. There are advantages to employing a commonly-used format, such as the 96-, 384- or 1536-well plate formats, as these, particularly the 8×12 96-well microtitre plate format, are compatible with a broad range of automation and software solutions. There are also advantages to using a linear array format, as the individual wells can be accessed then simply in a linear fashion, facilitating the implementation of certain robotics approaches. A close-to-linear format as disclosed in U.S. Pat. No. 5,490,415 [24] may have intermediate advantages. The benefits of the present invention can be realized using any of these array formats, and the choice as to which array format to employ in a particular case is generally made based on factors such as (i) the format(s) in which suitable lamina are available, (ii) compatibility with established automation and software solutions, and (iii) preferred volume and diameter of donor and receptor wells (guided by cross-talk considerations; engineering issues such as with bubble elimination, agitation, abstraction, lamina uniformity, reagent availability etc.). Associated with the chosen array format, the sample can comprise less than about 100 milligrams of the active component, preferably, less than about 1 milligram, more preferably, less than about 100 micrograms, and even more preferably, less than 100 nanograms. Preferably, the sample in a given well has a total volume of about 1-200 µl, more preferably about 5-150 µl, and most preferably about 10-100 µl.

Use of an array format, in addition to compactness, has the advantage that various automated methods of introduction samples are readily applied. Various automated distribution systems for simple liquids are commercially available, such as the MultiPROBE® II and MultiPROBE® EX, available from PerkinElmer Life and Analytical Sciences, Inc. of Boston, Mass. (las.perkinelmer.com), the Multiple Probe 215 and Constellation™ 1200 available from Gilson, Inc. of Middleton, Wis. (www.gilson.com), the Microlab STAR available from Hamilton Company of Reno, Nev. (www.hamilton-comp.com), the synQUAD available from Genomic Solutions (Cartesian Technologies) of Irvine Calif. (www.cartesiantech.com), the Tango™ available from Matrix Technologies Corp. (Robbins Scientific) of Sunnyvale Calif. (www.robsci.com), and the Genesis and Genesis NPS, available from Tecan, headquartered in Männedorf near Zurich, Switzerland (www.tecan.com).

Efficient assembly: A further benefit of the present invention is that the components of the apparatus, the printed circuit plate, the donor plate, lamina and receptor plate, can be assembled and held tightly together (so as to prevent leakage from a donor well or an acceptor well) by a simple inventive device. Previous implementations of array formats for testing the permeation of agents through a membrane have used simple screws as a means of connecting donor and receptor well plates and applying pressure to the interleaving membrane. This closure mechanism has major disadvantages in (i) reproducibility of the pressure being applied, (ii) uniformity of the pressure across the membrane surface, and (iii) time and convenience cost associated with applying and removing the bolts or screws. In one embodiment of present invention, two rectangular bars are employed to apply uniform pressure to the circuit wiring plate-donor plate-lamina-receptor plate assembly (FIG. 3 and FIG. 4). The cross bars are arranged, orthogonally to approximately bisect the circuit wiring plate, with the clamping screws positioned at the perimeter of the device, along lines that approximately bisect the circuit wiring plate.

In another embodiment, the circuit wiring plate (if present), donor plate, lamina, and receptor well plate assembly is held together, and pressure applied uniformly to the lamina to ensure sealing through the use of two opposing pressurized pillows. Such pillows are beneficially made of polyethylene, with a single feed port, and about 4"×6" in size when a standard microlitre plate footprint is employed for the donor well plate. The pillows may be filled or evacuated of a fluid; when filled the two pillows sandwich the test assembly between them, and distribute the pressure uniformly across the surface of the assembly, and hence the lamina. In a further embodiment, a floating clamp is used, that is, a clamp which rotates on a center point and which is then self aligning. Clamps are available from a number of suppliers, such as Sears, Roebuck and Co. of Chicago, Ill. (www.sears.com) and, before use in the present inventive apparatus, are beneficially modified so as to enlarge the clamping surface with a piece of rigid plastic, and to use an intermediate soft shoe, beneficially made of Durometer 60 rubber or similar material, that is at least about ¼" thick.

Complete well filling: A further benefit of the present invention is that it provides a means by which donor and/or receptor wells may be completely filled with fluid. Complete well filling is necessary if the MBSS system is to be reoriented during operation, such as may be desirable for making measurements at short sample contact times, or for sampling of the contents of wells during operation.

FIG. 5A also illustrates two cross-sectional view (511) of an illustrative arrangement according to the present invention. The apparatus comprises, as was illustrated also in FIG. 2, FIG. 3 and FIG. 4, a donor plate (530), and a receptor plate (515) sandwiching a lamina (514). The apparatus is equipped with a crossbar (517). The illustration at right (512) shows a perpendicular cross section of one two vertical pillars (518). The crossbar passes through holes (529) in the faces of two vertical pillars (518). A cylindrical rod (516) also passes through the vertical pillars through holes (531) in the pillars. By tightening clamping screws (519) mounted though the upper face of the vertical pillars a uniform clamping pressure may be applied to the circuit wiring plate (513), donor plate (530), lamina (514) and receptor plate (515), keeping this assembly together and ensuring sealing of the lamina at the perimeter of each donor well (524) and receptor well (527). In the embodiment illustrated in FIG. 5 are further provided with two channels (520) for locating pins which may be used to ensure correct and accurate alignment and registry of the various plates and lamina. Each donor well of the device is further provided with an electrode (522), together with an electrode retainer (523) and an overflow donor well compartment (521). This embodiment is further provided with O-rings (526) mounted in annular grooves (525) in the faces of the donor plate and the receptor plate adjacent to the lamina. O-rings are beneficially employed when the elasticity and sealing properties of the lamina are insufficient to ensure adequate sealing at the perimeters of each donor and receptor wells.

In this embodiment, the cylindrical rod (516) is mounted in a cylindrical channel through the receptor plate that runs parallel to, and directly beneath, a row of receptor wells. In the cylindrical rods (516) are provided a set of channels (532), in number and disposition such that there is one for each receptor well. In the FIG. 5A the channels (532) are aligned with the receptor wells. The cylindrical rod (516) may be rotated by means of a lever (533) to cause a seal in each of the receptor wells, as illustrated in FIG. 5B. If the device is inverted relative to the orientation depicted in FIG. 5A the channels in the bar will then be above the receptor wells. The receptor wells (527) may then be filled with fluid through the continuation of the receptor well on the other side of the rod (528), to a level part-way into the channels in the bar. Rotating the bar then seals the row of completely-filled receptor wells. The apparatus may then be re-inverted so that the receptor wells are beneath the lamina; the receptor well fluids remaining in complete contact with the lamina. The benefits of this Inventive apparatus are further evident in the description of use provided beneath.

Many variations of the apparatus depicted in FIG. 5A are possible. For example, the system may be provided with a smaller or larger number of donor and receptor wells than are shown in FIG. 5A. The system apparatus may take the form of a linear system as shown in FIG. 5A or may take the form of an array. Many other approaches to holding the assembly together may be taken including, for example, the approach shown in FIG. 6 and described below. It will also be appreciated that the use of electrodes in the donor wells is optional. It is also possible to make systems that utilize the cylindrical rod sealing system for both the donor and receptor wells. The rotation of the cylindrical bar may be accomplished by automated means, such as computer controlled motors or with the use of robotic arms.

Figure 6:
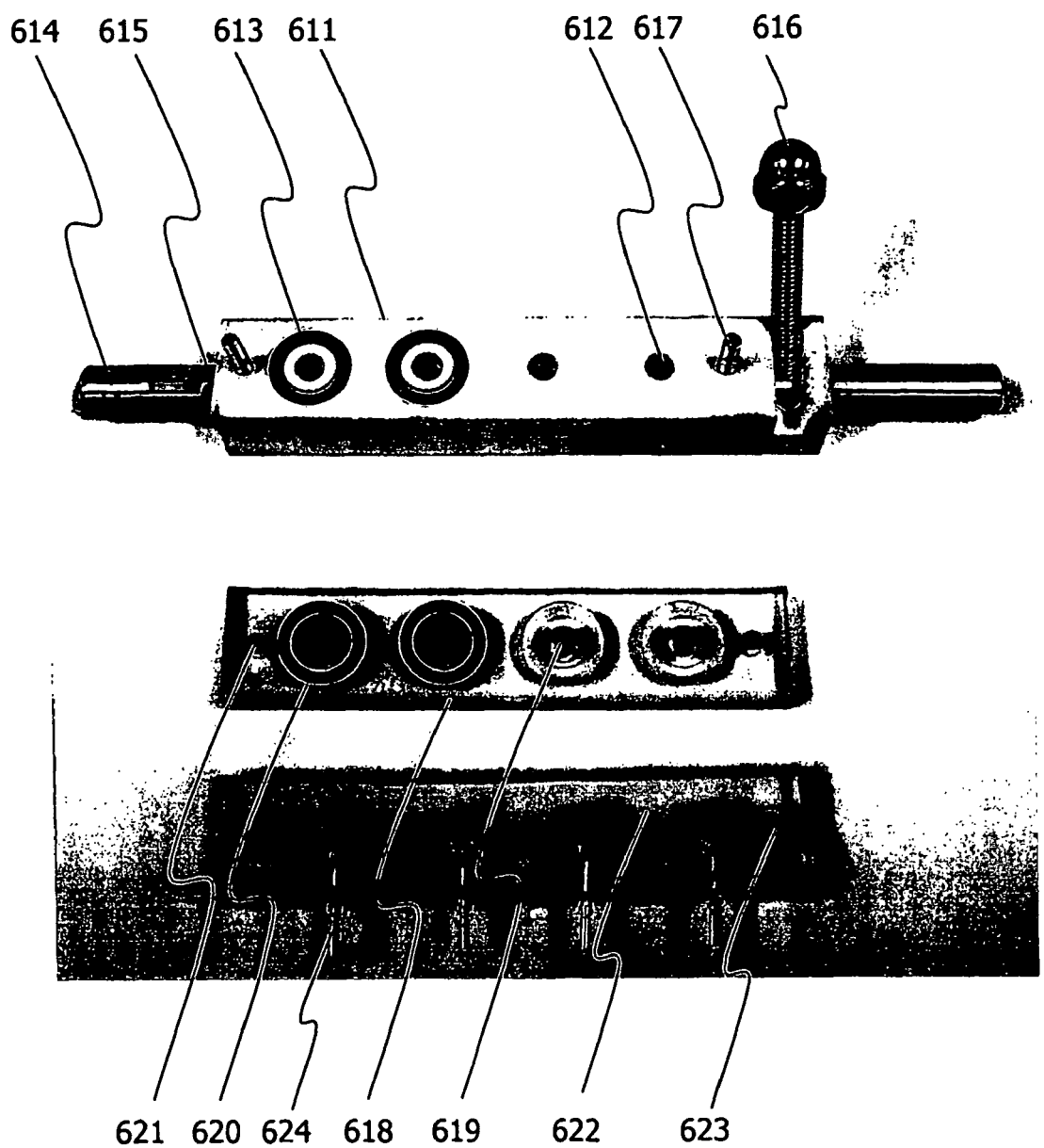
FIG. 6. Photograph of an embodiment of a circuit wiring plate-donor well plate-lamina-receptor well plate assembly, with device for ensuring complete receptor well filling, illustrating certain features.

For purposes of further illustration, FIG. 6 provides another depiction of the rotating rod mechanism of well sealing. A single row of four receptor wells (612) drilled in a Teflon block (611) is shown. Each is provided with a circumscribing annular slot, in which sits a circular O-ring (613). In a cylindrical channel drilled in the Teflon block, perpendicular to the receptor wells is provided a stainless steel rod (614), in which are drilled four parallel channels perpendicular to the rod. By means of a lever (616) the rod may be rotated so as to bring the channels in the rod into registry with the receptor wells, or so as to close the bottoms of the receptor wells by the rod perimeter. An alternative position for the lever, a tapped channel on the left hand side (615) is also shown. A donor plate (618) is produced from transparent polycarbonate. The donor plate contains also four donor wells (619), each circumscribed by an annular groove in which sits an O-ring (620). The donor plate is also equipped with two positioning holes (621), though which pass positioning and fastening screws (617) when the apparatus is assembled. The circuit wiring plate (622), is also equipped with positioning holes (623), and with a set of four holes that, on assembly, will sit one over each donor well, through which fluid may be introduced or removed from the donor well. Electrical connections (624) to which may be connected external leads, and to which electrodes placed in the donor wells will make electrical contact, are also provided. The operation of this embodiment is similar to that described above.

The rotating rod mechanism of ensuring complete well filling is an especially preferred embodiment. Several other mechanical means of achieving complete well filling that have benefits in particular cases, are also disclosed.

Referring now to FIG. 7, a sliding mechanism for complete well filling is depicted. FIG. 7A illustrates a receptor plate (713) provided with an array of straight-through channels (714). The receptor plate is beneficially made of Teflon or another polymer. In the illustration of FIG. 7A, above the receptor plate (713) is provided a sealing plate (711) that also has an array of straight through channels (712), the centers of which are arranged so as to align with the array of receptor wells when the sealing plate is suitably positioned. When placed against the receptor plate, the sealing plate forms a fluid-tight mating with the receptor plate, yet it may be moved laterally across the receptor plate surface. FIG. 7B and FIG. 7C illustrate how this sealing mechanism is used to provide complete well filling. In FIG. 7B is illustrated, in cross section, an assembly of a lamina (716) sandwiched between a receptor plate (713) and a donor plate (717), the receptor and donor plates being provided with mirror-related arrays of wells. Sealing plates are shown applied to the receptor plate side (711) and to the donor plate side (719). The receptor wells are filled with a fluid, in each case such that the uppermost level of the fluid (715) extends above the top of the receptor well and into the corresponding channel in the receptor sealing plate. After all receptor wells are so filled, the receptor sealing plate is shifted laterally, as shown in FIG. 7C, so that the section of the sealing plate (711) adjacent to the a given hole seals the corresponding receptor well. The fluid in excess of that needed to fill that receptor well is displaced with the receptor sealing plate (720) and may be removed by any of various means, such as an absorbent pad. The receptor wells themselves are then completely filled with the fluid and the apparatus may be inverted, while maintaining uniform contact between the fluid in each receptor well and the lamina. This embodiment is preferred when fluids more viscous that water are employed.

A further embodiment is illustrated in FIG. 8, which illustrates the use of a duck-billed valve, applied to each receptor well, to ensure complete well filling. An array of duckbill valves affixed to a plate with suitable holes serves as the receptor well plate (811), that is applied against a lamina (812). Each duckbill valve (such as can be obtained by custom manufacture from Da/Pro Rubber, Inc. of Valencia, Calif.; www.daprorubber.com) has a cylindrical base, which serves in this case as the receptor well, and a pair of 'beaks' or lips which meet to form a linear seal (817). The duckbill serves as a one-way valve. Thus, fluid may be introduced into the receptor well from a syringe (814) of which the needle (815) is inserted through the duckbill lips. As fluid is dispensed from the syringe, it progressively fills the receptor well until the receptor well is filled, at which point the excess fluid emerges through the duckbill lips, as shown in FIG. 8A. The syringe needle may now be removed, leaving the duckbill essentially fully filled with fluid. This embodiment is also preferred when fluids more viscous that water are employed. It is preferable to commence filling the receptor wells with fluid; to discontinue filling and then agitate the array, such as using a vortexing shaker, as well as to apply a slight negative pressure above the introduced fluid (which may be conveniently applied by inserting the needle of an empty syringe through the duckbill and extracting some air from the duckbill, or more preferably, to use a fluid handling robot to perform the fluid introductions and air extractions in an automated manner), so as to ensure that gas bubbles are eliminated, particularly from the receptor well fluid-lamina interface.

As illustrated in FIG. 8B, once the receptor wells are all completely filled, the apparatus may be inverted and the receptor well fluids will remain in contact with the lamina, as a the body of the duckbill (813) as well as the neck (816) remain fully filled with fluid.

A further advantage of the use of duckbill valves is that they may also be used for sampling of the fluid contents contained within the duckbill. In a preferred embodiment of the invention the duckbill contains an element that collapses readily. FIG. 8C illustrates a duckbill serving as a receptor well, in contact with a lamina (812). The duckbill contains a cylindrical, concertina element that collapses (and expands) readily in the vertical direction, similar to a bellows arrangement. The needle (819) of a syringe (818), or similar device, is inserted through the duckbill valve. Referring now to FIG. 8D, as the plunger of the syringe is slowly withdrawn, fluid is drawn from the inside of the duckbill into the syringe. Rather than creating a vacuum internal to the duckbill, the concertina region of the duckbill collapses as the fluid is removed. In this way the receptor well, the duckbill, remains full of fluid and without the introduction of air bubbles, although it's internal volume has been reduced. This embodiment is preferred for more viscous fluids.

Further embodiments are illustrated in FIG. 9 which depicts various other ways in which donor and/or receptor wells may be completely filled with fluid according to the present invention. The apparatus illustrated in FIG. 9 are preferably employed when the viscosity of the fluid to be introduced into or removed from the wells is generally in the range 5-500 centipoise. In FIG. 9A through FIG. 9F, objects such as balls are used to provide for well sealing.

In FIG. 9A a Teflon-coated object such as a sphere, comprised of a permanent magnet or a magnetizable material, serves to seal the bottom of a donor well. The well is filled in a configuration inverse to that depicted in FIG. 9A, as shown in FIG. 9B; once the well is filled to a level significantly beyond the start of the neck, a permanent magnet is applied to the end of the narrow section to cause the sphere to move to the neck (FIG. 9C). With the permanent magnet held in such position, the apparatus is inverted, the sphere remaining at the neck to seal the completely full receptor well (FIG. 9A). In cases where continued application of a permanent magnet to the receptor well bottom(s) is not an inconvenience, the receptor well(s) may again be filled in the configuration shown in FIG. 9B and, once filled to a level significantly up the narrower region, the permanent magnet is applied to lift the sealing sphere to the neck, where it will be retained by the permanent magnet.

In cases where it is inconvenient to operate a permanent magnet close to the well bottoms, or in cases where, for example, it is a requirement that both donor and receptor well arrays be fully filled, it may be convenient to use a spring-loaded object such as a ball, as illustrated in FIG. 9D and FIG. 9E. The well is filled in a configuration inverse to that depicted in FIG. 9D, as shown in FIG. 9E. The sealing object, the ball in this example, is displaced downward, stretching the spring, by a plunger or by a protrusion from the dispensing device. Once the well is filled with fluid to a level significantly above the start of the neck, the dispensing device tip is slowly removed and the spring then pulls the sealing object back into its sealing location at the neck, at which point the apparatus may be inverted to provide the configuration shown in FIG. 9D, with the well fully-filled. Other similar devices may be used. FIG. 9F uses a plunger affixed to the sealing object. The well is filled with fluid to a level significantly above the start of the neck, with the rod displaced downwards, as illustrated. Once the well is so filled, the rod is retracted slowly until the sealing object is seated in the sealing position at the neck. The apparatus may then be inverted, leaving the well completely filled.

In FIG. 9G is Illustrated another manner in which a duckbill-type well equipped with a collapsible concertina region may be employed. As shown in FIG. 9G, the well is filled with fluid using the methods generally introduced for duckbills above. After filling, and agitation to allow any gas bubbles that have been introduced, or not dispelled, to rise to the top of the well, the concertina region is compressed by an external plunger; the contents of the well are progressively expelled through the duckbill. The gas, being at the top is expelled first, followed by fluid. Once a reasonable amount of fluid has been expelled, the plunger is released. As the duckbill serves as a one-way valve, no fluid is able to get back into the well which then remains fully-filled.

Electrode arrays: Karande et al. [27,28] have disclosed the use of single-point skin conductivity as a proxy measure of the permeability of the stratum corneum, suitable for use in high throughput experimentation. Embodiments of the present invention support measurements of electrical conductance, but in an array format, with measurements of electrical response, and with fast, automated accumulation of electrical response data.

One embodiment is illustrated in FIG. 10. A donor well plate (1011) is provided with an array of donor wells (1012) shown, in FIG. 10A, partially filled with fluid. Each donor well is provided with an electrode (1017) that is electrically insulated from all of the other donor-well electrodes. Sandwiched between the donor well plate (1011) and a receptor well plate (1013) is a lamina (1015) with, on the receptor well side, an electrically conducting layer (1016) or an electrically conducting sheet or plate (1016). When full-thickness porcine skin is used as the lamina, the dermis is electrically conducting, so the dermal layer serves this purpose. The receptor well plate illustrated (1013) has a common receptor well (1014), filled with an electrically conducting fluid that is in contact with the lower surface of the conducting layer. In this example, if both the lamina (1015) and the electrically conducting sheet (1016) are permeable to a species provided in the donor wells, such species will diffuse from a given donor well, though the lamina and electrically conducting sheet, into the common receptor well. A common electrode (1018) is provided in the electrically conducting sheet (1016). Alternatively, in this illustrative embodiment, a common electrode may be provided in contact with the common receptor well fluid (1019). The donor and receptor well plates are beneficially fabricated from more or less rigid, and insulating plastic. The electrodes are preferably fabricated from wires of non-reactive metals, such as silver, platinum or gold, or may be a composite electrode such as silver/silver chloride (Ag/AgCl), depending on the specifics of the application, as will be well known to one skilled in the art. Where the lamina is a flexible material, such as skin or other tissue mechanical means to support to the lamina may be provided. Possible means for mechanically supporting the lamina include rigid permeable plates, rigid plates with holes (the holes preferably arranged to match the arrangement of the donor wells), suitably arranged posts in the receptor well, as well as combinations of the foregoing.

In the configuration shown in FIG. 10A, each of the donor well electrodes (1017) is beneficially connected via wiring on a circuit wiring plate (as shown as 216 in FIG. 2) to a connector mounted on the circuit wiring plate. A mating connector is then beneficially applied to this connector, to enable an electrical connection to be made from each donor well electrode, as well as from the common electrode, to a multichannel switch, the output of which is provided to a digital multimeter (suitable components are available from National Instruments Corporation of Austin, Tex.; www.ni.com). In a preferred embodiment, the multichannel switch and digital switch are provided in a chassis that may be controlled by a computer, using control software such as developed in LabVIEW (available from National Instruments Corporation of Austin, Tex.; www.ni.com) and which provides also for electronic storage of the electrical conductance or electrical response data so generated. Once the data are stored electronically, they are beneficially imported into an informatics environment which provides for coupling of these data with other information about the experiments, such as fluid sample preparation recipes and characterization, as well as for data visualization, manipulation, interpretation and archiving.

Another preferred embodiment is illustrated in FIG. 10B. A donor well plate (1011) is provided with an array of donor wells (1012) shown, in FIG. 10B, partially filled with fluid. Each donor well is provided with an electrode (1017) that is electrically insulated from all of the other donor-well electrodes. Sandwiched between the donor well plate (1011) and a receptor well plate is a lamina (1015) that, compared to FIG. 10A, is lacking a highly electrically conductive base sheet. The receptor well plate is provided with an array of receptor wells matching the donor well array (1020), here shown completely filled with fluid as achieved according to the methods of the present invention described above. Each receptor well is here provided with a separate electrode. Electrical connections are provided from each pair of electrodes (that in the donor well and that in the corresponding receptor well) to a multichannel switch and, thence to a digital multimeter. Secondly, the electrode array is arranged for simple, fast and robust establishment of electrical connections with the measurement circuitry (FIG. 14) as the experiment is prepared.

In a further embodiment of the present invention, measurements of the electrical response of a lamina in contact with samples that can be solids, soft materials, or poorly electrically conductive media are possible by the application of a gel, or similar, electrode directly to an area of lamina exposed in each well, rather than through the indirect electrical contact made with the electrode is in contact with fluid in a donor well such as is illustrated in FIG. 10A and FIG. 10B.

Another preferred embodiment is illustrated in FIG. 10C. A donor well plate (1011) is provided with an array of donor wells (1012) shown, in FIG. 10B, partially filled with fluid. Each donor well is provided with a pair of electrodes (1022 and :1023) that are mounted into the donor well plate (1011) and not in direct physical contact with the donor well fluid. In this configuration electrical impedance measurements can be made over the 100 Hz-10 MHz frequency range, according generally to the methods described by Rigaud et al. [32] and Dowdeswell at al. [33], and changes in the electrical response of the stratum corneum as a function of the nature and duration of application of a test fluid monitored. From these changes the degree to which constituents in the test fluid are affecting the barrier properties of the lamina can be inferred. This contactless method is preferred for poorly electrically conducting test fluids and may simplify experimentation; electrodes that are in contact with a test fluid medium generally need to be discarded or carefully cleaned between successive experiments.

Other methods of sampling: In another embodiment of the present invention, the effect of a test formulation on the lamina is gauged by off-line analysis of the lamina, after it has been exposed for a certain period of time to the test formulation. It is generally preferred that an array of formulations is applied for the same duration to a lamina, so that lamina samples may be prepared for off-line analysis in a parallel manner. By way of illustration, the apparatus depicted in FIG. 10C might be used. A different formulation is applied to each donor well, together with a suitable number of replicates, blanks and controls, either simultaneously, using the methods of the present invention described beneath, or at a time that is recorded. The formulations are allowed to remain in contact with the lamina for the target duration and the donor well formulations then removed, either simultaneously, or at a sequence of times so as to ensure a constant time of application for each donor well. The receptor well plate is removed. A cylindrical plug of lamina is then punched from the region of lamina in contact with each donor well, preferably by means of a parallel punch set-up in which an array of punches is provided on a press, the array being identical in layout to that of the donor well array. Each plug of lamina is then analyzed separately. Where the measurement is directed to the uptake of a material by the lamina, a radiolabelled form of the material may be applied to the donor well, and the plug of lamina produced after the application dissolved in a suitable medium, combined with scintillation cocktail and then counted using a liquid scintillation counter. Where porcine, murine or human skin is used as the lamina, the plugs may be dissolved in SOLVABLE™, an aqueous based solubilizer (available from PerkinElmer Life and Analytical Sciences, Inc., of Boston, Mass.; http://las.perkineimer.com/cataloq).

Another beneficial off-line analysis method, suitable for indicating disruption of the lamina in cases such as where the lamina is skin, is ultrasonic spectroscopy. Following exposure of the lamina to a sample for an appropriate time, a plug of the lamina is removed and placed in an ultrasonic spectrometer, such as is available from Ultrasonic Scientific of Piscataway, N.J. (www.ultrasonic-scientific.com). Ultrasonic waves propagate through opaque biological tissues and recent instrumentation developments have improved the resolution and the limitations on sample size to an extent that useful information on stratum corneum structure can be derived from ultrasonic measurements. More preferably, the skin is sliced into rectangles prior to application of the test formulation, by the methods of the present invention described above, and the pre-cut rectangles then provided after application of the test formulation to the ultrasonic spectrometer. This method reduces the likelihood of complications in the analysis from disruption of the skin barrier by the process of punching to produce plugs.

Sampling exfoliation: The present inventive method and apparatus enable measurement of the degree to which a test formulation affects the exfoliation of surface material on a lamina, such as is desirable in the development of improved emollients for personal care applications in the case of skin as the lamina. The apparatus generally depicted in FIG. 10C may be employed, but in which the array of electrodes (1022 and :1023 in FIG. 10C) may be omitted or simply not used. To each of the donor wells is applied a formulation, including a suitable number of replicates, blanks and controls. Also introduced into each donor well is a number of small objects; identical ball bearings are preferably used. The apparatus is placed on a vortexing mixer such that the objects impinge and roll across the surface of the lamina. The amount of material that is lost from the lamina surface into each donor well is then determined by performing an analysis on the donor well fluid. In the case of skin, by way of example, a standard 8×12 96-fold microtitre plate array of donor wells is applied to a single piece of defrosted pig skin and the apparatus (FIG. 10C) assembled. Into each donor well is introduced either PBS, as the control (8 wells); or one of 11 test emollient formulations (8-fold replicates of each). Into half of each set of donor wells are introduced three 2 mm diameter stainless steel bearing balls (such as are available from Boca Bearing of Boynton Beach, Fla.; www.bocabearinas.com). The apparatus is mounted on a high-speed orbital mixer (such as the TEOS 150 available from TechElan LLC of Mountainside, N.J.; www.techelan.com) and the speed of the mixer adjusted so that the bearing balls in each of the wells are driven across the surface of the skin forming the bottom of that well. After completion of the agitation, a sample of the fluid in each donor well is taken and subjected to analysis for keratin concentration, using generally the methods described by Fraser et al. [34]. A greater tendency of a given test formulation to promote exfoliation is indicated by greater keratin concentrations in the donor wells containing such a test formulation relative to the controls, most especially for the donor wells not supplied with the bearing balls.

Depth profiling of permeation into a lamina or layer-by-layer analysis: A further embodiment of the present invention provides for performing, in an automated fashion, a layer-by-layer analysis of the lamina after application of a test formulation. A schematic illustration of an apparatus used to remove successive layers from a lamina, that is exemplary but not limiting, is provided in FIG. 11A. The lamina (1111) is placed on a table (1112) which can be translated, in the direction of the straight arrow, by a suitable motor (1116), mechanically coupled to the table (1115). A roller (1113) is equipped with an adjustable tensioning device to ensure that the roller is applied to the lamina with a uniform pressure. The exterior surface of the roller is provided with a sheet of one-sided sticky tape. The diameter of the roller is selected such that its circumference is somewhat greater than the length of the lamina, so that each region on the lamina will be contacted by a different area of the one-sided sticky tape. The roller is further provided with a means in which the sheet of one-sided sticky tape can be readily replaced, such as by providing the tape on the outside of a cylinder which is easily mounted and dismounted from the roller. Various roller diameters may be used, to accommodate various lamina sizes. The roller is beneficially provided with a drive mechanism (1114) whereby the translation of the table (1112) is coupled to the rotation of the roller (1113) to ensure that the one-sided sticky tape is uniformly applied to and then peeled from the surface of the lamina.

As the table (1112) translates and the roller (1113) rotates, the sticky side of the tape is applied to the lamina, as it is uniformly passed beneath the roller, and each area on the lamina is contacted by a different area of sticky tape. Reference marks can be applied to the tape to ensure that a position on the tape can be referenced back to the corresponding position on the lamina surface. Alternatively, a reference material or materials can be applied to the lamina before stripping to provide suitable reference marks on the tape. Once the lamina has passed completely underneath the roller, the roller is lifted and the tape piece is removed; a dean piece of one-sided sticky tape, sticky side towards the outside of the roller, is then provided (such as by replacing a cylinder with one-sided sticky tape applied on the outside of the roller).

The base and lamina are repositioned back at the start of travel, the roller is replaced, and the process is repeated the desired number of times. The set of tape pieces applied to the lamina then contains, in sequence, the set of layer abstractions from the lamina. The individual tape pieces may then be analyzed in any established way, such as by direct chemical analysis, spectroscopically or otherwise. When radiolabelled components are used in a sample, extracts from the tape strips may be counted in a suitable scintillation counter.

An especially preferred embodiment is illustrated in FIG. 11B. In this embodiment, the lamina (1117) is affixed to a roller (1118) with a circumference beneficially somewhat larger than the length of the lamina. By mechanical means, the perimeter of the roller (1118) is caused to press against a tape (1123), with suitable adhesive on one side, that is provided from a supply roll (1119). The rotations of supply roll, roller and the translation of the tape (1123) are coupled to ensure that the deposit onto the tape (1123) is a faithful image of the lamina surface. The tape (1123) is wound onto a second spool (1121) and, beneficially, an inert, non adhesive protecting film, such as made of Teflon or polypropylene, is wound over the exposed surface of the tape (1123) to ensure that what has been removed from the lamina does not contaminate the back of a different region of the tape. This embodiment (FIG. 11B) has an advantage that successive strippings can be taken from the lamina simply by continued rotation of the roller and spools.

In both of the embodiments illustrated in FIG. 11, it is obvious that the regions of the surface of a lamina that were in contact with differing test formulations applied to the lamina, as in employing the apparatus illustrated in FIG. 2 through FIG. 6 or FIG. 10, will correspond accordingly to different regions on the sticky tape strip and then the analysis of the stripped regions can then be linked unambiguously to a given position on the lamina and hence to a particular donor well, and to its associated test formulation.

The embodiment of the inventive apparatus illustrated in FIG. 11A and FIG. 11B is beneficially applied to lamina that have successive outer layers, one or more of which can be removed by this tape stripping operation; such is the case for porcine, murine and human skin. Where such is not the case, the sticky tape removal mechanism is beneficially replaced by another mechanism, such as microtoming, suitable for the particular material of the lamina.

Figure 12:
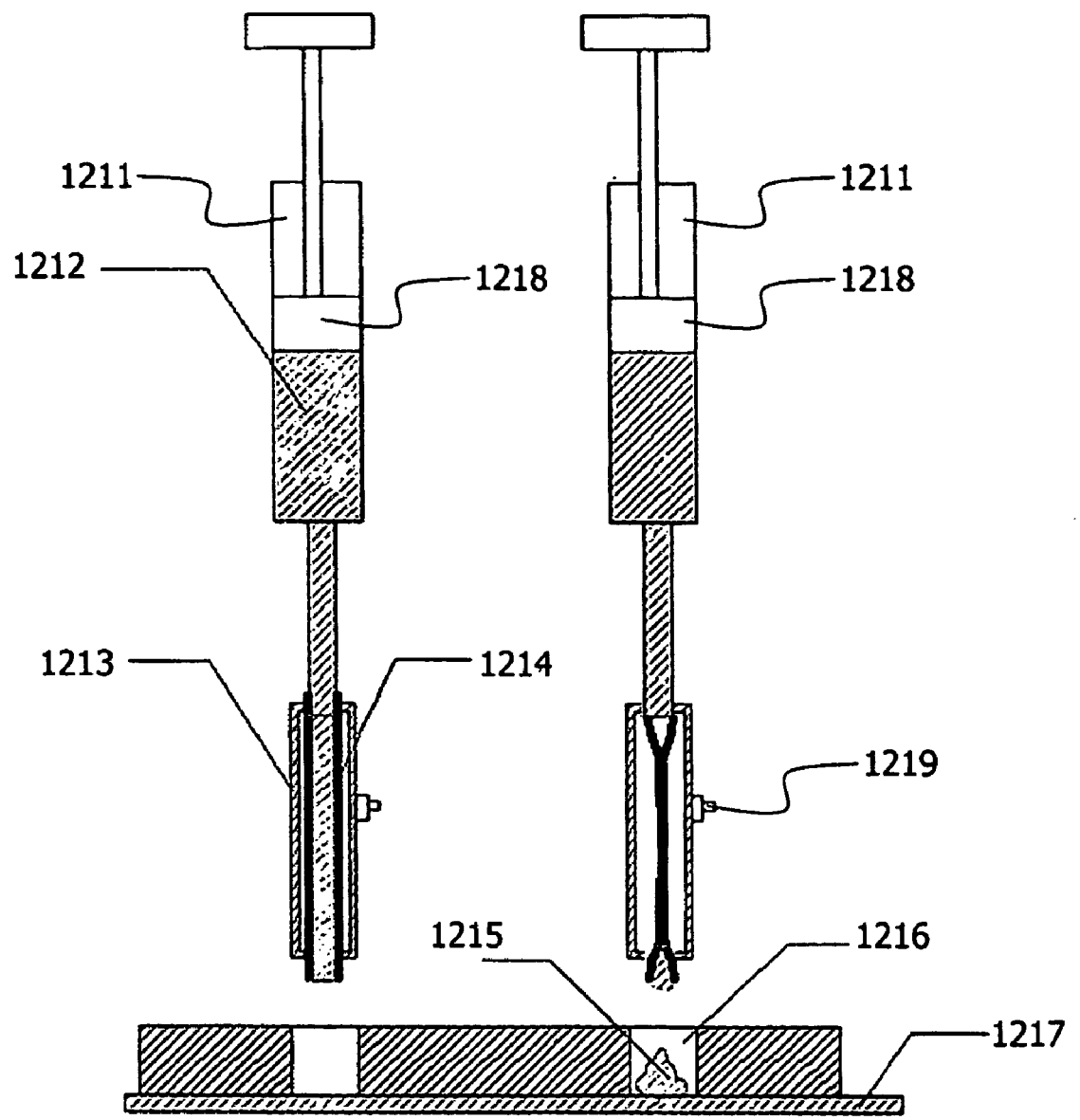
FIG. 12. Schematic diagrams of an apparatus used to apply a viscous soft material to a donor or receptor well.

Application and manipulation of complex samples: A further embodiment of the inventive apparatus suitable for the application of a soft material, as a sample or as a sample component, to a lamina is illustrated in FIG. 12. The soft material to be dispensed, generally with a viscosity in the range 100-70,000 centipoise, is loaded into a syringe with a wide needle (1211), any manner of which might be used provided that, for the viscosity of the soft material, the diameter of the needle is sufficient that flow through the needle occurs when reasonable pressure is applied to the plunger, either manually or by an automated pump; the syringe may be manually or, preferably, automatically activated, such as by a syringe pump. When the plunger (1218) is depressed, soft material is expelled from the wide syringe barrel (1212), into a device that comprises a flexible and collapsible tube (1214) mounted inside a rigid casing (1213). The collapsible material is preferably fabricated from a material such as Teflon for which the soft material has a low interfacial energy. The region inside the casing that is outside the tube may be pressurized by introduction of fluid through an inlet (1219). As the fluid is introduced the tube begins to collapse, the syringe plunge is held fixed, and the soft material contained within the collapsible tube is forced out of the end of the tube and into or onto the intended dispensation target, in this case a donor well (1216) in a donor well plate applied to a lamina (1217). Advantageously, the pressurizing fluid inlet (1219) is disposed off-center, closer to the syringe needle that the collapsible tube exit, as illustrated in (FIG. 12).

This asymmetry helps to ensure that the bulk of the soft material in the tube is dispensed. Advantages of the embodiment illustrated in FIG. 12 are that the wide barrel of the syringe is effectively covered, preventing evaporative loss or chemical degradation on exposure to the atmosphere, in addition to the function of the apparatus to cut off the dispensed amount of viscous soft material which, otherwise, would tend simply to hang from the syringe when the plunger motion stops.

An additional complication with viscous samples, those with a viscosity above about 100 centipoise, is an increased likelihood of establishing air pockets, particularly at the sample-lamina interface. In a further embodiment, such air pockets can be eliminated by the application of vigorous orbital shaking, or of ultrasonic agitation to an individual well or, preferably to the entire array of wells. Suitable ultrasonication baths are available from many suppliers such as Nickel-Electro Limited of Weston Super Mare, UK (www-.martex.co.uk/blwa/nickel/ultra.htm), and Branson Ultrasonics Corporation of Danbury, Conn. (www.bransonultrasonics.com).

In a further embodiment, one or more of vigorous orbital shaking, ultrasonic agitation, or the introduction of a mechanical stirrer are beneficially applied to disrupting the microstructure of soft material samples. Many skin lotions are emulsions or reverse emulsions and the process of rubbing the lotion onto the skin has the effect of disrupting the droplet microstructure or 'breaking' the emulsion, liberating the emulsion droplet contents. Effective screening of such skin lotion formulations may be performed with the present inventive apparatus by using such agitation mechanisms to generate mechanical shear so as to break the emulsion before skin penetration or absorption screens are applied.

Description of Application and Measurement Types

Workflow: With the present inventive apparatus and methods, developments of a range of types are possible, as illustrated generally in FIG. 1. The stage termed "Implement screening protocol; provide membrane, test formulations; complete experimentation stages; analyze results" (13 in FIG. 1) is, for one illustrative embodiment, elaborated further in FIG. 13.

The stage commences with detailed planning of the experimentation efforts (1311), Initially based on decisions as to the details of the lamina that will be used, how the lamina need to be stored and treated prior to measurement, the sourcing of the lamina, that is from where the lamina will be obtained and under what conditions they will be harvested or provided. Next, the protocol(s) by which the inventive apparatus will be applied to measurements of modification of barrier properties are determined (1312); this step beneficially also includes some work applied to validating these determined protocols in application to a number of known materials or standards, so that the suitability of the protocols for the planned application is proven and so that the various apparatus and equipment are checked and calibrated suitably.

Next, the details of which test formulations are to be produced and evaluated is determined (1313). Thus process generally involves decisions as to the breadth of test formulation composition and processing parameters that will be considered, and to the sampling algorithms that will be used to select which specific test formulations will be produced, and in which sequence. For illustration, in the case of binary combinations of skin CPE's, these decisions will entail choices as to which individual CPE's will be employed, what increments in mole fraction of each constituent CPE in the binary will be sampled, and what total CPE concentrations will be considered, as generally described by Karande et al. [12], Incorporated herein by reference. Also determined are the number of replicates, blanks and control samples that will be included.

The decisions as to which test fluids to evaluate (stage 1313) is beneficially assisted by various design of experiment algorithms and software, such as provided in Statistica (available from StatSoft, Inc. of Tulsa, Okla.; http://www.statsoft-inc.com/), Quantisweb available from (available from Quantis Formulation Inc. of Montreal, Quebec, Canada; http:// www.quantisweb.com/), MINITAB® Release 14 (available from Minitab Inc. of State College, Pa.; www.minitab.com), STATGRAPHICS® Plus available from StetPoint, LLC of Englewood Cliffs, N.J. (www.statpoint.com) or the various methods disclosed in [35-39] each incorporated herein by reference.

With completion of the experimentation plan and schedule, the program proceeds to the next set of four stages (1314 though 1317 in FIG. 13) in which the inventive apparatus and methods are applied to successive test formulation libraries. A library of test formulations is provided (1314), produced by any suitable method as will be well known to one skilled in the art. The library of test formulations is next introduced into the inventive apparatus, and various processing and measurement steps are applied (1315), as are detailed further following. After completion of these processing and measurement steps, various samples, such as the lamina or part(s) of the lamina, or donor and/or receptor well contents) are collected and provided to off-line analyses, as desired (1316). To complete the planned library set will, in general, take more than one iteration through steps 1314, 1315 and :1316, so that at the completion of :1316, a decision is made as to whether assessment of the library set is complete (1317), in which case the program will proceed to analysis and interpretation of the cumulative data. If not, steps 1314, 1315 and :1316 will be effected for the next test formulation library in the determined sequence. Generally, some visualization, analysis and interpretation of the accumulated data are performed prior to completion of the assessment of the full library set.

Screening of skin barrier modification by electrical conductance change: In a program to evaluate the effect of constituents in each element of a library of formulations on the barrier properties of skin, the apparatus illustrated in FIG. 3 and FIG. 4 may be beneficially applied. By way of example, a receptor plate, with an 8 by 12 array of separate, round-bottom wells of 200 µl volume, 6.5 mm well diameter, in the standard microtitre plate footprint, is provided, each well in which is loaded with pH 7.4 phosphate buffer saline (PBS, phosphate concentration=0.01M, NaCl concentration=0.137M; available from Sigma-Aldrich Inc., www.sigmaaldrich.com). A piece of porcine skin is applied, with the dermal side in contact with the PBS in each of the array of receptor wells. Porcine skin can be harvested from Yorkshire pigs and stored at −70° C. immediately after procurement until the time of experiments. The skin is thawed at room temperature prior to each experiment. A piece of porcine skin slightly larger than 4½" by 3" is chosen, so that all of the receptor wells are fully covered by the skin. The filling of the receptor wells with PBS ensures that the skin remains hydrated over the entire duration of the experiment (in this specific example, where it is not necessary to analyze the receptor well contents at the end of the experiment, a receptor plate design that provides a common receptor bath, in place of an array of separate receptor wells, might be beneficially employed). A donor well plate, also with an 8 by 12 array of separate wells in the standard microtitre plate format and footprint, with straight-through wells, and a flat plate bottom, is applied next to the porcine skin, flat plate bottom in contact with the outermost layer of the skin, the stratum corneum. On top of the donor well plate is placed a circuit wiring plate and the apparatus clamped tightly together by means of the tensioning screws (as are illustrated in FIG. 3 and FIG. 4). Based on the design of the test formulation library, a sample formulation is then introduced into each of the 96 donor wells. This design will generally provide for a number of test formulations being introduced into donor wells distributed across the donor well array, together with a suitable number of replicates, references and blanks. A replicate is a composition in a donor well identical to that in another donor well, with the number and positioning in the donor well array of the replicates of a given composition chosen so as to provide the desired checks and measurement statistics. A blank is a donor well that is left unfilled, or which is filled with a composition that is missing the compound to be monitored. A reference is a composition for which permeation rate has been separately measured and which, therefore, can be used as a reference. The donor wells are filled by introducing a pipette tip through the fill-holes provided in the circuit wiring plate. The additional air-release holes that are also provided in the circuit wiring plate help avoid issues with blow-back or pressurization. Electric connections to one or more signal generators, to one or more switches such as a reed relay multiplexer, and thence to a digital multimeter are made, by connecting suitable male RS232 plugs to the female RS232 plugs on the circuit wiring plate (FIG. 4). Data polling is commenced such that a conductance measurement is made for each of the 96 electrodes in turn, with a data accumulation time per well, and a time to complete measurements of all 96 wells of, by way of illustration, some 0.1 sec and some 10 sec respectively. If the initial current is found to be greater than a predetermined threshold value, it is assumed that the skin area between the corresponding donor and receptor wells is defective and the data accumulated from that well are then discarded and not used in subsequent analyses. The data may be accumulated continuously over a 4 h, 6 h, 8 h, 12 h, 24 h or 48 h period, or preferably are accumulated in discrete time windows such as every hour or every 4 h after the experiment is commenced. After completion of the data accumulation, the data are analyzed to yield measurements of the change in conductance at a given time, $t_1$, relative to that at the start of conductance measurements, $t_0$. Using the methods described in Mitragotri et al. [27,40], incorporated herein by reference, the modification in the barrier properties of the skin in contact with each of the donor well formulations with time may then be deduced.

This methodology is beneficially applied when the impact of all of the formulations on the barrier properties is relatively slow, such that there will be little change in the conductance values over the time required to complete introduction of the donor well samples and initiate electrical conductance or impedance measurements. A further embodiment is beneficially applied when there is the possibility of a more rapid change in barrier properties. After assembling the apparatus, yet before introduction of samples into the donor wells, the necessary electrical connections are made and the polling of the conductance values of each well in sequence is commenced. As there is no conducting material in any of the donor wells, the impedance values measured in this polling are extremely high. At this point the filling of the donor wells is commenced. Once conducting material is introduced into a donor well such that electrical contact is made between the electrode and the area of the stratum corneum exposed in that well, there is an immediate and sharp reduction in the measured impedance. This change is logged in the accumulating impedance data; the time for initial contact of the donor well sample with the skin in that well, $^j t_0$, is then identified by the time at which the sharp change in impedance is observed. Filling of all of the donor wells with their requisite samples can then proceed, with, in each case the $^j t_0$, time for the specific well signaled by the sharp change observed in the impedance measurements for that well. Thus, the $^j t_0$, values for all of the wells may differ somewhat, depending on whether wells are filled individually by a manual pipette or by a fluid dispensing robot for which a single dispensing needle is used, or whether a group of wells is filled at the same time by application of an 8- or 16-fold manual pipette, or a 96-fold fluid dispensing robot, for example. However, a precise for each well can be defined. For a still more precise value of $^j t_0$, rather than performing a polling sweep of each of the 96 electrodes in sequence, the impedance measurements may be limited during the well-filling operations to a subset of wells, or to a single well, in consort with the dispensing operations, as will be obvious from this overall description.

In both of these embodiments, after completion of the electrical impedance measurements over the desired experimentation period, the contents of donor and receptor wells and of the lamina may be analyzed to provide additional information, according to common methods and as described further below.

In a further embodiment, where it is desirable to have direct side-by-side comparisons between different samples, the present inventive methods and apparatuses provide for simultaneous contact of all donor well samples with the lamina. This may be achieved, in one embodiment, by using a dispensing robot that has a number of dispense heads equal to, or greater than, the number of wells in the donor array and then arranging for simultaneous dispensing into all donor wells.

In a further embodiment, a donor well plate, with an 8 by 12 array of separate, straight-through wells in the standard microlitre plate footprint is provided; underneath the donor well plate is provided a circuit wiring plate which, in addition to providing an electrode in each donor well, serves to seal the bottom of each donor well (in this embodiment the donor well plate is not equipped with holes, such provided in the earlier example in which the donor wells were filled by introducing test formulations through the circuit wiring plate). The requisite sample is applied to each donor well through its open end (that will subsequently be brought into contact with the lamina), in an amount which is sufficient to fill the donor well up to no more than some 80% of the donor well height and with no superfluous sample on the top donor plate surface between wells. Once all donor wells are so loaded, a piece of porcine skin is provided as the lamina, sufficient in area to ensure that all of the donor wells are covered, with some additional margin so that a good seal around each donor well will be achieved. The piece of skin is oriented such that the side of the stratum corneum contacts the donor plate. As no donor well is more that some 80% filled, no contact between a donor well sample and skin occurs at this point in the assembly. A receptor well plate, with an 8 by 12 array of separate wells in the standard microtitre plate footprint, equipped with a set of 8 rods underlying each row of 12 receptor wells is provided, according to the configuration illustration in FIG. 5 and FIG. 6, and the tensioning screws are applied to as to seal the perimeters of the receptor wells and of the donor wells against the skin. All 8 rods are rotated to the position in which a channel through the rod aligns with a corresponding receptor well, effectively extending such receptor well through the channel in the rod. Rotation of the set of 8 rods may be performed manually, according generally to the illustration in FIG. 6, and, still more preferably, the rotation of the rods may be performed by an automated means such as using a set of motors, or a single motor with suitable coupling devices, under computer control. PBS is then introduced into each of the array of receptor wells, in quantity sufficient to completely fill the receptor wells themselves and to partially fill the cylindrical channel in the rod that sits above the receptor well. Once all receptor wells have been so filled, the set of 8 rods is then rotated some 90° so that the receptor well is then sealed at its top by the rod (and the cylindrical channels, each containing the excess of receptor well PBS, are then in contact with neither the receptor wells, nor the outside of the assembly) (FIG. 5 and FIG. 6). As all receptor wells are fully filled, when the apparatus is now inverted such that the receptor wells are uppermost, the PBS in each receptor well remains in uniform contact with the skin. The assembled apparatus is then inverted, so as to bring the donor wells uppermost and receptor wells lowermost, and to allow the sample in each donor well to flow down so as to make contact with the skin. Beneficially, the assembled device is then placed on an orbital shaker so as to agitate each of the donor wells and ensure that the air in each donor well is dislodged from the skin-donor sample interface and prompted to rise to the top of the donor well, then ensuring uniform contact of the donor sample with the surface of the area of skin exposed to that donor well. This time of inversion, the time of first contact of donor well samples with the skin, is then taken as the $t_0$ time for the electrical conductance measurements.

In a further embodiment, a vacuum may be applied to a donor well or to a set of donor wells so as to prompt degassing of the donor sample and the dislodgment of any gas bubbles from the lamina-donor sample interface. Referring again to the immediately preceding example, the circuit wiring plate might additionally be equipped with a removable seal, such as a polymer or metal film applied across its external surface, such that when the assembled apparatus is inverted to bring the circuit wiring plate uppermost, with the donor well plate immediately beneath it, the seal may be removed and an attachment to a vacuum applied across the entire circuit wiring plate. Application of the vacuum is beneficially applied progressively and with care, to avoid blow-out of any donor well sample. The application of mild vacuum can beneficially be combined with the use of an orbital mixer and/or ultrasound. In further embodiments, individual wells or subsets of wells are provided with removable or penetrable seals, such as septa, for the purposed of applying a mild vacuum to prompt sample degassing and gas bubble dislodgement from the lamina-donor sample interface.

In a further embodiment, non-contact electrical impedance measurements over the 100 Hz-10 MHz frequency range may be accumulated, using procedures for filling receptor and donor wells and for accumulated data from the instant of donor well sample contact with the skin similar to those just described and apparatus as depicted in FIG. 10C, according generally to the methods described by Rigaud et al. [32] and Dowdeswell at al. [33].

Direct measurements of entity permeation: In a further embodiment, direct measurement of the permeation of a target species from a donor well through a lamina such as a skin sample into a receptor well is made, in addition to or in replacement for the measurements of electrical conductance or impedance which signal the change in the barrier properties of the lamina. Such a direct measurement of permeation is desirable, for example, (a) to calibrate the modification of barrier properties signaled by the impedance change, (b) to compare the extent of delivery into the lamina versus through the lamina, (c) to quantify the permeability of a specific molecule through the lamina, (d) to allow the present inventive apparatus and methods to be applied to cases of permeabilization that may not be signaled by a pronounced change in the electrical impedance of the lamina, or (e) for experiments in which the donor sample is only poorly conductive. For direct measurements of entity permeation, it is desirable to perform analytical measurements of the receptor well contents, at some time interval(s) after a donor sample contact to the skin is commenced.

For simplicity, the simultaneous accumulation of electrical impedance measurements is not included in this illustrative description, although how such measurements would simultaneously be made will be obvious to one skilled in the art based on the above description. A donor well plate, with an 8 by 12 array of separate wells in the standard microtitre plate footprint, equipped with a set of 8 rods underlying each row of 12 donor wells is provided, according to the configuration illustration in FIG. 5 and FIG. 6. All 8 rods are rotated to the position in which a channel through the rod aligns with a corresponding donor well, effectively extending such donor well through the channel in the rod. Rotation of the set of 8 rods may be performed manually, according generally to the illustration in FIG. 6, and, still more preferably, the rotation of the rods may be performed by an automated means such as using a set of motors, or a single motor with suitable coupling devices, under computer control. A piece of skin, sufficient in size to cover all of the donor wells, is placed on the bottom of the donor well plate, and a receptor well plate, with an 8 by 12 array of separate straight-through wells in the standard microtitre plate footprint is then applied beneath the skin piece and the assembly clamped together by tightening of the tensioning screws. The library of 96 donor well samples, selected according to the design criteria using the methods described above, is then introduced into the array of donor wells, in quantity sufficient to completely fill the donor wells themselves and to partially fill the cylindrical channel in the rod that sits above the donor well. The time of first contact of the donor well sample to the skin is recorded as the $^j t_0$ for that particular donor well. Once all donor wells have been so filled, each of the 8 rods is then rotated some 90° so that the donor well is then sealed at its top by the rod (and the cylindrical channels, each containing the excess of donor well fluid, are then in contact with neither the donor wells, nor the outside of the assembly) (FIG. 5 and FIG. 6). As all donor wells are fully filled, when the apparatus is now inverted such that the receptor wells are uppermost, the contents of each donor well remain in uniform contact with the skin. Each receptor well is now filled with a measured amount of PBS. For convenience, the uppermost ends of the receptor wells are left open or, to prevent accidental introduction of contaminants or dust, they may be covered with a plate or with a material such as Parafilm M® Barrier Film (available from laboratory supply companies, such as SPI Supplies and Structure Probe, Inc. of West Chester, Pa.; www.2spi.com).

After an appropriate time interval, an aliquot of the fluid in each receptor well is extracted using a pipette, which may be a single needle manual pipette, an 8- or 12-fold multipipette, or the needle of a fluid handling robot. When more than one extraction is to be made from a given receptor well in a given experiment, it is important that the amount of receptor sample removed on each extraction be accurately recorded, so that suitable corrections for permeate amounts removed can be made. Further, if, in aggregate, a substantial proportion, that is greater than some 60%, of the sample in a given receptor well is to be removed, it is beneficial to replenish that receptor well content by addition of a determined amount of receptor fluid, PBS in this specific example. Such replenishments may be necessary following each receptor well sample extraction and, in each case, the amount of fluid reintroduced into each receptor well needs to be accurately recorded so that calculations of permeate concentrations can be made suitably.

After receptor well sample extraction, each extracted aliquot of receptor fluid is then provided to a suitable analytical measurement, such as is well known to one versed in the art. For example, where the permeate of interest is, in each case, a colored molecule, the amount of permeate in each receptor well sample may be quantified by providing the set of receptor well samples, dispensed one into each well in a microlitre plate, to a plate reader. Other suitable measurement techniques include, but are not limited to, infrared spectroscopy, near Infrared spectroscopy, Raman spectroscopy, or nuclear magnetic resonance ("NMR"). Where a high performance liquid chromatography ("HPLC") protocol has been developed for the permeate, the receptor well sample aliquots may beneficially be provided in sample vials, to be introduced into the autosampler of an HPLC system. Beneficially, a parallel HPLC system that provides for the simultaneous analysis by HPLC of 4, 6, 8, 12, 24 or some other multiplicity of samples, might be employed, so that the HPLC measurements do not become excessively rate-limiting relative to the experimentation work low. Suitable parallel HPLC systems are available, for example, from Shimadzu Corporation of Kyoto, Japan (www.shimadzu.com), SEPIAtec GmbH of Berlin, Germany (www.sepiatec.com), and Nanostream, Inc. of Pasadena, Calif. (www.nanostream.com).

Passive permeabilities of an active component through a lamina, such as a skin piece, can also be measured using trace quantities of a radiolabelled active component. According to known methods, radiolabelled active components are rotary evaporated in order to remove any solvent in which they are shipped and any tritium which had reverse exchanged into it. The radiolabelled active component is then redissolved in a suitable solvent and combined into, or redissolved directly within each of various sample compositions, including enhancers, carriers, additives, and/or other excipients, to a typical concentration of 1 μCi/ml. The mixtures are beneficially prepared separately and added to the donor wells, as described above. The concentration of the radiolabelled active component in each of the receptor wells is measured by extracting a sample from each receptor well as described above, combining a known volume of this sample with a suitable scintillation cocktail and then providing the combination to a scintillation counter (e.g., TopCount NXT available from PerkinEimer Life and Analytical Sciences, Inc. of Boston, Mass. (las.perkinelmer.com)).

In a further embodiment, the relative rates of permeation through a lamina of a test compound from each of a library of formulations are determined by initiating commencement of contact between each of the donor well formulations and the lamina, and hence of potential commencement of penetration through the lamina, at essentially the same time and then monitoring, on the receptor side of the lamina opposite each donor well, the emergence of the corresponding compound as a function of time after this initial contact. This embodiment employs the apparatus and method for achieving both complete receptor well sampling, and simultaneous contact of each of a set of donor formulations with the lamina described above. By way of illustrative example, into each of a set of donor wells is placed a given concentration of a hydrophilic drug dissolved in a water-ethanol mixture, together with a combination of chemical penetration enhancers ("CPEs"). Each donor well receives a combination of CPEs according to a design, based on a useful sampling of the CPE combination space, together with a suitable number of replicates, references and blanks, as described generally above. The contents of all donor wells are simultaneously brought into contact with the lamina, using the method and apparatus described above, and from that experiment start time, $t_0$, the opposite side of the lamina, or the receptor wells are monitored by an analytical method or device suitable for indicating the amount of the test compound, that is the hydrophilic drug, that has permeated through the lamina. This analytical device might use any known method, such as detection of color by UV-vis spectroscopy, detection of fluorescence, binding to an agent to generate color or fluorescence etc. By way of example, the color of a receptor well fluid may be monitored by means of a fiber optic cable affixed to the bottom of the receptor well and connected to a suitable spectrometer. As is well known to one skilled in the art, such use of fiber optic cables allows measurements from an array of samples to be performed rapidly. From the time taken for the test compound to permeate through the lamina and be detected on the receptor well side, the permeation rate can be deduced.

The permeability values can be calculated under steady-state conditions from the relationship $P=(dN_r/dt)/(AC_a)$ where A is the surface area of the lamina accessible to a sample, $C_a$ is the concentration of the active component in the sample, and $N_r$ is the cumulative amount of active component which has permeated through the lamina into the receptor well. There is significant inter-species and inter-individual variability in skin permeability; for example, an inter-individual variation in human skin of 40% is reported by Williams, et al. [41]. The passive permeability enhancement, $E_P$, is calculated relative to the passive permeability from PBS according to Eq. (1).

$$E_P = \frac{P_{(enhancer)}}{P_{(PBS)}} \quad (1)$$

where $P_{(enhancer)}$ is the permeability of the active component in the presence of the other sample constituents, and $P_{(PBS)}$ is the permeability of the active component from PBS. The fluxes from saturated solutions, $J^{sat}$, are calculated from $J^{sat}=P\,C^{sat}$, where $C^{sat}$ is the drug solubility in the sample formulation. Flux enhancements, $E_j$ are calculated using Eq. (2), $$E_j = \frac{J^{sat}_{(enhancer)}}{J^{sat}_{(PBS)}} \quad (2)$$

where $J^{sat}_{(enhancer)}$ and $J^{sat}_{(PBS)}$ are the fluxes of active component from saturated solutions of enhancer and PBS, respectively.

It is understood that the methods and apparatus described above for complete filling of an array of receptor wells, and for sampling the contents of each of an array of receptor wells, can be applied to an array of receptor wells, and array of donor wells, or simultaneously to arrays of both donor and receptor wells. Further the methods and apparatus may be applied to a subset of wells in a well array. Further, the apparatus employed for achieving complete filling of the receptor wells in the above example might, depending on the specifics of the application, be replaced by one or more of the devices for allowing complete well filling and well sampling illustrated in FIG. 7, FIG. 8 and FIG. 9.

Further analyses subsequent to best formulation contact with a lamina: In addition to the accumulation of measurements of the electrical impedance of the lamina at the position of each donor well, or direct measurement of the concentration of a test substance in the each of the array of receptor wells, the amount of a test substance in each of the array of donor wells may be analyzed, using methods and apparatus similar to those described above in the case of receptor well sampling.

In a further embodiment the concentration of a test substance layer by layer through a lamina is measured. According to the present invention, this is conveniently achieved in an array format using the inventive apparatus shown in FIG. 11A or FIG. 11B. At the end of the experiment duration, the circuit wiring plate, if present, is removed, the contents of all donor wells are removed by aspiration and both the wells and the lamina surface exposed in each well are gently washed with water, water-alcohol mixture or PBS. The clamp and the receptor plate are removed and the bottom surface of the lamina is gently washed with water, water-alcohol mixture or PBS. The apparatus is inverted and the donor array plate removed. The lamina is then placed on the base of the stripping-roller device (FIG. 11A or FIG. 11B) and successive layers are removed from an area on the lamina encompassing the positions of several donor wells, typically of all donor wells. Successive adhesive sheets or successive sections in an adhesive sheet then contain successive layers through the lamina. Depending on the nature of the test substance, the adhesive sheets or samples taken from the adhesive sheets may be analyzed by any known method. For example, infrared spectroscopy, near infrared spectroscopy, Raman spectroscopy, NMR, UV-vis spectroscopy, or fluorescence spectroscopy might beneficially be applied. Where the test substance is provided in a radiolabelled form, an instrument suitable for counting the radioactivity of the samples might be employed. In each case of analytical experiments, to optimize experimentation efficiency it is beneficial to arrange for the analytical measurements to be made in a fast serial or parallel manner, such as using an array or plate reader.

In a further embodiment, a direct analysis of the concentration of a test substance in the lamina, or in the lamina as remains after application of one or more tape-stripping operations, is made by punching-out a piece of the lamina that was exposed to a test formulation in a donor well, digesting the piece of lamina in a suitable solvent, such, in the case of skin, SOLVABLE™ (available from PeridnElmer Life and Analytical Sciences, Inc., of Boston, MA; http://las.perkinelmer.com/cataloq) then subjecting the remains to analysis by any known method.

Device rotation: The present inventive method and apparatus for achieving air pocket- and bubble-free well loading enable permeation and other skin impact assessment experiments to be performed in further ways. If both the donor wells and receptor wells are completely filled according to the methods and apparatus described above, then the assembled apparatus, comprising circuit wiring plate-donor well plate-lamina- and receptor well plate, may be moved, or orientated in any fashion without disturbing the contact of either donor or receptor samples with the lamina. Thus permeation experiments may be performed with the receptor well array uppermost, with the donor well array uppermost, with donor and receptor arrays vertical, or at any other angle. Additionally, the apparatus can be shaken or agitated without affecting the sample contact with the lamina, greatly extending the utility of screening experiments. Samples that contain components that would otherwise cream or settle can be used; exfoliation experiments with an in situ agitation may also be performed, and so on, as will be obvious to one skilled in the art.

Screening of exfoliation: In a further embodiment, the degree to which exfoliation, or the loss of material from the surface of a lamina, is promoted by a test substance in a sample may be assayed. By way of example, a receptor plate, with an 8 by 12 array of separate, round-bottom wells of 200 µl volume, 6.5 mm well diameter, in the standard microtitre plate footprint, is provided, each well in which is loaded with pH 7.4 PBS. A piece of porcine skin is applied with the dermal side in contact with the PBS in each of the array of receptor wells, the area of the piece of skin being sufficient that all of the receptor wells are fully covered by the skin. A donor well plate, also with an 8 by 12 array of separate wells in the standard microtitre plate format and footprint, with straight-through wells, and a flat plate bottom, is applied next to the porcine skin, flat plate bottom in contact with the outermost layer of the skin, the stratum corneum. Based on the design of the test formulation library, a sample pre-mixed formulation is then introduced into each of the 96 donor wells and the initial contact time for each well, $^j t_0$, recorded. The apparatus is mounted on a high-speed orbital mixer. For each of a subset of the donor wells, after a preselected time interval following $^j t_0$ three 2 mm diameter stainless steel bearing balls (such as are available from Boca Bearing of Boynton Beach, Fla.; www.bocabearings.com) are introduced into the donor well and the apparatus agitated on the orbital shaker for a determined time period, such as 10 secs, 30 secs, 1 min, or other. The speed of the mixer is set so that the bearing balls will, for all of the wells into which they are introduced, be driven across the surface of the skin forming the bottom of that well. After completion of the agitation, the fluid in that donor well is analyzed so as to provide the amount of the lamina that has been exfoliated from the lamina into the donor well. This analysis may be performed by any suitable analytical method. For example, in the case of skin as the lamina, a sample may be taken from the given donor well and subjected to analysis for keratin concentration, using generally the methods described by Fraser et al. [34] or to an analysis for protein concentration, such as is well-known to one skilled in the art. By way of further example in the case of skin as the lamina, a fiber-optic light source and detector may be introduced into the well and the amount of sloughed-off cells or cell clusters assessed by the increase in turbidity of the donor well medium. For each of the donor wells chosen for mechanically-assisted exfoliation analysis according to the experiment design, at the preselected time for each well, the process of introducing the three bearing balls, agitating and analyzing donor well sample, is repeated. The experiment design is determined so that the effect of a test substance in a formulation on the tendency of material to be exfoliated from the stratum corneum is provided, as a function of time (based on using a set of donor wells, each provided with a similar formulation, but for which the preselected times before exfoliate analysis differ), and degree of mechanical abrasion (based on comparing data from two or more donor wells provided with the same formulations, after the same preselected time intervals, but for a subset of which exfoliation was assayed after agitation with the bearing balls while for a further subset bearing balls were not applied) can be assessed.

General application comments: The methods and devices of the present invention have a number of beneficial applications, for example, to develop (I) optimal compositions or formulations comprising one or more active components and one or more inactive components for achieving desired characteristics for such compositions or formulations, (ii) optimal adhesive/enhancer/excipient compositions for compatibility with an active component or drug, (iii) optimal active component or drug/adhesive/enhancer/additive compositions for maximum drug flux through stratum corneum, (iv) optimal active component or drug/adhesive/enhancer/additive compositions to minimize cytotoxicity.

Although the description above contains many specificities, this should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. NO claim element herein is to be construed under the provisions of 35 U.S.C. 112, sixth paragraph, unless the element is expressly recited using the phrase "means for."

CITATIONS

[1] Bellhouse B J, Kendall M A F: Dermal Powderject device. In *Modified-release drug delivery technology*. Edited by Rathbone M J, Hadgraft J, Roberts M S: Marcel Dekker; 2003:607-617.

[2] Levy A: Intraject: prefilled, disposable, needle-free injection of liquid drugs and vaccines. In *Modified-release drug delivery technology*. Edited by Rathbone M J, Hadgraft J, Roberts M S: Marcel Dekker; 2003:619-631.

[3] Pass F, Hayes J: Needle-free drug delivery. In *Modified-release drug delivery technology*. Edited by Rathbone M J, Hadgraft J, Roberts M S: Marcel Dekker; 2003:599-606.

[4] Prausnitz M R, Mitragotri S, Langer R: Current status and future potential of transdermal drug delivery. *Nature Reviews Drug Discovery* 2004, 3:115-124.

[5] Bos J D, Meinardi M M H M: The 500 Dalton rule for the skin penetration of chemical compounds and drugs. *Exp. Dermatol.* 2000, 9:165-169.

[6] Cevc G, Gebauer D, Stieber J, Schatzlein A, Blume G: Ultraflexible vesicles, Transfersomes, have an extremely low pore penetration resistance and transport therapeutic amounts of insulin across the intact mammalian skin. *Biochim. Biophys. Acta* 1998, 1368:201-215.

[7] Müller R H, Mäder K, Gohla S: Solid lipid nanoparticles (SIGN) for controlled drug delivery—a review of the state of the art. *Eur. J. Pharm. Biopharm.* 2000, 50:161-177.

[8] Honeywell-Nguyen P L, Bouwstra J A: The in vitro transport of pergolide from surfactant-based elastic vesicles through human skin: a suggested mechanism of action. *J. Control. Release* 2003, 86:145-156.

[9] Touitou E, Dayan N, Bergelson L, Godin B, Eliaz M: Ethosomes—novel vesicular carriers for enhanced delivery: characterization and skin penetration properties. *J. Controlled Release* 2000, 65:403-418.

[10] Santus G C, Baker R W: Transdermal enhancer patent literature. *Journal of Controlled Release* 1993, 25:1-20.

[11] Williams A C: *Transdermal and topical drug delivery: From theory to clinical practice*. London, Chicago: Pharmaceutical Press; 2003.

[12] Karande P, Jain A, Mitragotri S: Discovery of transdermal penetration enhancers by high-throughput screening. *Nature* (Biotechnology) 2004, 22:192-197.

[13] Foldvari M, Baca-Estrada M E, He Z, Hu J, Attah-Poku S, King M: Dermal and transdermal delivery of protein pharmaceuticals: lipid-based delivery systems for interferon alpha. *Biotechnol. Appl. Biochem.* 1999, 30:129-137.

[14] Juhlin L, Evers H: EMLA: a new topical anesthetic. *Advances in Dermatology* 1990, 5:75-92.

[15] Elias P M, Feingold K R, Thornfeldt C R: Lipids for epidermal moisturization and repair of barrier function. U.S. Pat. No. 5,643,899, 1997.

[16] Leyden J J, Rawlings A V (Ed): *Skin Moisturization* Carol Stream, Ill.: Allured Publishing Corp.; 2002.

[17] Ghyczy M, Vacata V: Hydroxyacids. In *Skin Moisturization*. Edited by Leyden J J, Rawlings A V: Allured Publishing Corp.; 2002:323.

[18] Franz T J: The finite dose technique as a valid in vitro model for the percutaneous absorption in man. In *Skin: Drug Application and Evaluation of Environmental Hazards (Current Problems in Dermatology,* Vol. 7). Edited by Simon G, Paster Z, Klingberg M, Kaye M: S. Karger; 1978:58-68. vol 7.]

[19] Bronaugh R L, Stewart R F: Methods for in vitro percutaneous absorption studies IV: the flow-through diffusion cell. *J. Pharm. Sci.* 1985, 74:64-67.

[20] Bronaugh R L, Collier S W: In vitro methods for measuring skin permeation. *Cosmetics & Toiletries* 1990, 105: 86-93.

[21] Moody R: Automated In Vitro Dermal Absorption (AIVDA): Predicting skin permeation of atrazine with finite and infinite (swimming/bathing) exposure models. *Toxicology in Vitro* 2000, 14:467-474.

[22] Ussing H H, Zehran K: Active transport of sodium as the source of electric current in the short-circuited isolated frog skin. *Acta Physiol. Scand.* 1951, 23:110-127.

[23] Grass G M: Device and method for circulating fluid over a membrane. U.S. Pat. No. 5,599,688, 1997.

[24] Mak V H W, Francoeur M L: Diffusion test apparatus and method. U.S. Pat. No. 5,490,415, 1996.

[25] Selick H E, Smith G A, Tolan J W: Multi-well single-membrane permeation device and methods. U.S. Pat. No. 6,043,027, 2000.

[26] Cima M J, Chen H, Gyory J R: System and Method for Optimizing Tissue Barrier Transfer of Compounds. WO 02/06518 A1, 2002.

[27] Mitragotri S, Karande P: A Combinatorial Method for Rapid Screening of Drug Delivery Formulations. WO 02/16941A2, 2001.

[28] Karande P, Mitragotri S: High Throughput Screening of Transdermal Formulations. *Pharmaceutical Research* 2002, 19:655-660.

[29] Audus K L, Bartel R L, Hidalgo I J, Borchardt R T: The use of cultured epithelial and endothelial cells for drug transport and metabolism studies. *Pharm Res.* 1990, 7:435-451.

[30] Naughton G K, Naughton B A: Three-dimensional skin culture system. U.S. Pat. No. 5,266,480, 1993.

[31] Gennaro A R (Ed): *Remington: The Science and Practice of Pharmacy.* 19th Edition Pennsylvania: Mack Publishing Company; 1995.

[32] Rigaud B, Hamzaoul L, Frikha M R, Chauveau N, Morucci J P: In vitro tissue characterization and modelling using electrical impedance measurements in the 100 Hz-10 MHz frequency range. *J. Physiological Measurement* 1995, 16 (Suppl. 3A):A15-A28.

[33] Dowdeswell R M, Payne P A, Amrani M E N: Impedance measurements of bodily matter. U.S. Pat. No. 6,690,181, 2004.

[34] Fraser R D B, MacRae T P, Rogers G E: *Keratins: their composition, structure, and biosynthesis*. Springfield, Ill.; 1972.

[35] Newsam J M, Freeman C M, Yao T: High Throughput Experimentation: The Role of Simulation. *Chemistry Today* (Gendai Kagaku) 1998, 1998:31-37.

[36] Newsam J M: Design of Catalysts and Catalyst Libraries. In *Combinatorial Catalysis and High Throughput Catalyst Design and Testing (NATO Science Series C*: Vol. 560). Edited by Derouane E G, Lemos F, Corma A, Ribeiro F R: Kluwer; 2000:301-335.

[37] Strehlau W, Newsam J M, Demuth D, Richert W, Brenner A, Schunk S A, Klein 3: Computer-aided optimization of substance libraries. WO Patent 01/97152A2 (and German Patent DE 100 28 875 A1), 2001.

[38] Demuth D, Finger K-E, Hill J-R, Levine S M, Löwenhauser G, Newsam J M, Strehlau W, Tucker J, Vietze U: Developing Computational Support for High Throughput Experimentation Applied to Heterogeneous Catalysis. In *Combinatorial Materials Development (ACS Symposium Series No.* 814). Edited by Malhotra R: American Chemical Society; 2002:pp. 147-164.

[39] Cawse J N (Ed): *Experimental Design for Combinatorial and High Throughput Materials Development* New York, N.Y.: Wiley; 2003.

[40] Mitragotri S, Karande P, Jain A: Penetration Enhancer Combinations for Transdermal Delivery. U.S. patent application Ser. No. 10/625,195, 2003.

[41] Williams A C, Cornwell P A, Barry B W: On the non-Gaussian distribution of human skin permeabilities. *Int. J. Pharmaceutics* 1992, 86:69-77.

What is claimed is:

1. An apparatus for assaying effects of test formulations on barrier properties of at least one piece of skin, comprising:
   a first plate including
      a plurality of first wells configured so that a first end of each of the first wells is sealable with the at least one piece of skin, the first wells each including openings at a second end that allow a first plurality of formulations to be introduced or removed, wherein at least a portion of the first wells are arranged linearly in a row, and
      a generally cylindrical plate channel that runs generally parallel to the row of the first wells positioned between the first and second ends thereof;
   a generally cylindrical rod mounted in the plate channel of the first plate and extending lengthwise along a longitudinal axis, the rod including a plurality of rod channels that are generally perpendicular to the longitudinal axis, wherein each of the rod channels is configured to be in general alignment with a respective one of the first wells in the row, wherein the rod is rotatable about the longitudinal axis between an open position in which the rod channels allow the first plurality of formulations to be introduced or removed through the openings of the first wells in the row, and a closed position in which the rod retains the first plurality of formulations in the first wells and promotes contact between the first plurality of formulations in the first wells and the at least one piece of skin independently of an orientation of the apparatus; and
   a second plate configured for assembly with the first plate so that the at least one piece of skin may be sandwiched between the first and second plates, the second plate including
      a plurality of second wells, wherein each of the second wells is in general alignment with a respective one of the first wells on an opposite side of the at least one piece of skin, each of the second wells including a first end sealable with at least one piece of skin and openings at a second end that allow a second plurality of formulations to be introduced or removed.

2. The apparatus of claim 1, further comprising mechanical means for sealing the second wells after the second plurality of formulations have been introduced or removed through the openings.

3. The apparatus of claim 2, wherein the mechanical means for sealing the second wells comprise at least one selected from the group consisting of: magnetic or magnetizable spheres; one or more rotating rods; one or more sealing plates; spring-loaded balls; and sealing balls affixed to plungers.

4. The apparatus of claim 1, further comprising a plurality of electrodes for measuring electrical conductance or impedance of the at least one piece of skin, wherein each of the electrodes is configured to be associated with a respective one of the first and second wells when assembled so that once the first and second wells are filled each of the electrodes contacts the test formulation in the respective one of the wells.

5. The apparatus of claim 1, further comprising a circuit wiring plate mountable to one of the first and second plates, the circuit wiring plate including a plurality of electrodes for measuring electrical conductance or impedance of the at least one piece of skin, wherein each of the electrodes is configured to be associated with a respective one of the wells when assembled so that once the first and second wells are filled each of the electrodes contacts the formulation in the respective one of the wells.

6. The apparatus of claim 5, wherein the circuit wiring plate comprises an array of holes through each of which the test formulations may be introduced or removed.

7. An apparatus for assaying effects of formulations on barrier properties of at least one piece of skin, comprising:
a donor plate including a plurality of donor wells arranged in an array, each of the donor wells including a first end sealable with the at least one piece of skin, and top openings at a second end through which a first plurality of formulations may be introduced or removed;
a receptor plate mountable to the donor plate to sandwich the at least one piece of skin therebetween, the receptor plate including a plurality of receptor wells arranged in an array, each of the receptor wells including a first end sealable with the at least one piece of skin, and bottom openings at a second end through which a second plurality of formulations may be introduced or removed; and
a sealing device configured to seal the top and bottom openings to retain the formulations in the donor and receptor wells and promotes contact between the formulations and the at least one piece of skin independently of an orientation of the apparatus.

8. The apparatus of claim 7, wherein the sealing device comprises a rod mounted in the receptor plate.

9. The apparatus of claim 8, wherein the rod is movable between an open position allowing the second plurality of formulations to be introduced or removed through the bottom openings and a closed position in which the rod generally seals the receptor wells.

10. The apparatus of claim 9, wherein the rod comprises a plurality of rod channels each alignable with a respective one of the receptor wells to allow the second plurality of formulations to be introduced or removed through the bottom openings when in the open position.

11. The apparatus of claim 10, wherein the rod is rotatable between the open and closed positions.

12. The apparatus of claim 7, wherein the sealing device comprises magnetic or magnetizable balls.

13. The apparatus of claim 7, wherein the sealing device comprises at least one of: one or more sealing plates; spring-loaded balls; and sealing balls affixed to plungers.

14. The apparatus of claim 7, wherein the sealing device comprises a collapsible element and a one-way valve, whereby gas or liquid may be expelled from respective wells through the one-way valve and cause the collapsible element to correspondingly collapse so that the respective wells remain generally full of the formulations and without the introduction of air bubbles.

15. The apparatus of claim 7, further comprising a plurality of electrodes arranged in an array for measuring electrical conductance or impedance of the at least one piece of skin, wherein each of the electrodes is configured to be associated with a respective one of the donor wells when assembled so that once the wells are filled each of the electrodes contacts the formulation in the respective one of the donor wells.

16. The apparatus of claim 7, further comprising a circuit wiring plate mountable to the donor plate, the circuit wiring plate including a plurality of electrodes arranged in an array for measuring electrical conductance or impedance of the at least one piece of skin, wherein each of the electrodes is configured to be associated with a respective one of the donor wells when assembled so that once the wells are filled each of the electrodes contacts the formulation in the respective one of the donor wells.

17. The apparatus of claim 16, wherein the circuit wiring plate comprises an array of holes through each of which the test formulations may be introduced or removed.

18. The apparatus of claim 7, wherein a one of the donor plate and the receptor plate comprises a set of elongate and generally parallel slots configured for allowing a blade to cut the at least one piece of skin when sandwiched between the donor and receptor plates, each of the slots disposed generally intermediate of adjacent rows of the wells in the array of the one of the donor plate and the receptor plate.

19. The apparatus of claim 18, wherein the other of the donor plate and the receptor plate comprises a set of grooves generally arranged in mirror image fashion to the slots, so that the blade introduced through the slots can pass completely through the at least one piece of skin and into the grooves.

20. The apparatus of claim 7, wherein the donor and receptor plates each comprise a set of elongate and generally parallel slots configured for allowing a blade to cut the at least one piece of skin when sandwiched between the donor and receptor plates, so that the blade can be introduced through the slots from either side of the at least one piece of skin, each of the slots disposed generally intermediate of adjacent rows of the wells in a respective array.

21. The apparatus of claim 7, further comprising a plurality of O-rings mounted in annular grooves of the donor and receptor plates adjacent the first ends of each of the donor and receptor wells, the O-rings configured to ensure sealing at perimeters of each of the donor and receptor wells at the at least one piece of skin.

22. A method of assaying effects of a first plurality of formulations on barrier properties of at least one piece of skin, comprising:
assembling a donor plate and a receptor plate to sandwich the at least piece of skin therebetween, wherein the at least one piece of skin generally seals bottom openings of a plurality of donor wells of the donor plate and top openings of a plurality of receptor wells of the receptor plate;
introducing a second plurality of formulations to the receptor wells so that second plurality of formulations contact the at least piece of skin from the receptor wells;

sealing the receptor wells to retain the second plurality of formulations in the receptor wells and promote contact between the second plurality of formulations and the at least one piece of skin;

inverting an orientation of the assembled donor and receptor plates;

introducing the first plurality of formulations to the donor wells so that the first plurality of formulations contact the test membrane from the donor wells;

obtaining samples from the first plurality of formulations and/or the second plurality of formulations; and analyzing the samples to assess the effects of the first plurality of formulations on the barrier properties of the at least one piece of skin.

23. The method of claim 22, further comprising sealing the donor wells to retain the first plurality of formulations in the donor wells.

24. The method of claim 22, further comprising, after the assembling step and before the step of introducing the second plurality of formulations to the receptor wells, inverting an orientation of the assembled donor and receptor plates.

25. An apparatus for assaying effects of formulations on at least one piece of skin, comprising:

a donor plate including a plurality of donor wells arranged in an array, each of the donor wells including a first end sealable with the at least one piece of skin, and top openings at a second end through which a first plurality of formulations may be introduced or removed;

a receptor plate mountable to the donor plate to sandwich the at least one piece of skin therebetween, the receptor plate including a plurality of receptor wells arranged in an array, each of the receptor wells including a first end sealable with the at least one piece of skin, and bottom openings at a second end through which a second plurality of formulations may be introduced or removed; and mechanical means for sealing the donor and receptor wells to retain the formulations in the donor and receptor wells independently of an orientation of the apparatus.

26. An apparatus for assaying effects of test formulations on at least one test membrane, comprising:

a donor plate including a plurality of donor wells arranged in an array, each of the donor wells including a first end sealable with the test membrane, and top openings at a second end through which the test formulations may be introduced or removed;

a receptor plate mountable to the donor plate to sandwich the test membrane therebetween, the receptor plate including a plurality of receptor wells arranged in an array, each of the receptor wells including a first end sealable with the test membrane, and bottom openings at a second end through which the test formulations may be introduced or removed; and a sealing device configured to seal the top and bottom openings to retain the test formulations in the donor and receptor wells independently of an orientation of the apparatus, wherein the sealing device comprises magnetic or magnetizable balls.

27. An apparatus for assaying effects of test formulations on at least one test membrane, comprising:

a donor plate including a plurality of donor wells arranged in an array, each of the donor wells including a first end sealable with the test membrane, and top openings at a second end through which the test formulations may be introduced or removed;

a receptor plate mountable to the donor plate to sandwich the test membrane therebetween, the receptor plate including a plurality of receptor wells arranged in an array, each of the receptor wells including a first end sealable with the test membrane, and bottom openings at a second end through which the test formulations may be introduced or removed; and a sealing device configured to seal the top and bottom openings to retain the test formulations in the donor and receptor wells independently of an orientation of the apparatus, wherein the sealing device comprises a collapsible element and a one-way valve, whereby gas or liquid may be expelled from respective wells through the one-way valve and cause the collapsible element to correspondingly collapse so that the respective wells remain generally full of the test formulation and without the introduction of air bubbles.

\* \* \* \* \*